United States Patent
Al-Lamee et al.

(10) Patent No.: US 6,599,558 B1
(45) Date of Patent: Jul. 29, 2003

(54) TREATING METAL SURFACES TO ENHANCE BIO-COMPATIBILITY AND/OR PHYSICAL CHARACTERISTICS

(75) Inventors: Kadam Gayad Al-Lamee, Leeds (GB); Yousef Samih Taktak, Matlock (GB)

(73) Assignee: Polybiomed Limited (GB)

( * ) Notice: Subject to any disclaimer, the term of this patent is extended or adjusted under 35 U.S.C. 154(b) by 0 days.

(21) Appl. No.: 09/452,697

(22) Filed: Dec. 2, 1999

Related U.S. Application Data

(63) Continuation-in-part of application No. PCT/GB98/01609, filed on Jun. 3, 1998.

(30) Foreign Application Priority Data

Jun. 3, 1997 (GB) .............................. 9711377

(51) Int. Cl.[7] .............................. B05D 1/36; B05D 3/10; B05D 5/04; A61L 27/00; A61L 27/54

(52) U.S. Cl. .................. 427/2.24; 427/2.1; 427/2.28; 427/407.1; 427/409; 427/301; 427/302; 427/327; 427/340

(58) Field of Search .................. 427/2.1, 2.24, 427/2.28, 407.1, 409, 301, 302, 327, 340

(56) References Cited

U.S. PATENT DOCUMENTS

| | | | |
|---|---|---|---|
| 3,634,123 A | | 1/1972 | Eriksson |
| 5,229,172 A | | 7/1993 | Cahalan et al. |
| 5,336,518 A | | 8/1994 | Narayanan et al. |
| 5,344,455 A | | 9/1994 | Keogh et al. |
| 5,356,433 A | | 10/1994 | Rowland et al. |
| 5,607,475 A | * | 3/1997 | Cahalan et al. ............. 424/422 |
| 5,625,083 A | * | 4/1997 | Bezuglov et al. ........... 549/467 |
| 6,013,855 A | * | 1/2000 | McPherson et al. ....... 427/2.24 |
| 6,143,037 A | * | 11/2000 | Goldstein et al. ........... 424/422 |

FOREIGN PATENT DOCUMENTS

| | | |
|---|---|---|
| WO | 9117046 | 11/1991 |
| WO | 9504839 | 2/1995 |
| WO | 9707834 | 3/1997 |

OTHER PUBLICATIONS van der Giessen, et al. "Heparin Coated Coronary Stents: From Bench to Patient", pp. 169 175.

Larm et al. "A New Non–Thrombogenic Surface Prepared by Selective Covalent Binding of Heparin Via a Modified Reducing Terminal Residue", Biomat., Med. Dev., Art. Org., 11(2&3) (1983), pp. 161–173.

(List continued on next page.)

*Primary Examiner*—Bret Chen
*Assistant Examiner*—Jennifer Kolb Michener
(74) *Attorney, Agent, or Firm*—Baker Botts LLP

(57) ABSTRACT

A metal, glass or ceramics surface is treated to enhance its compatibility with biological material such as blood or blood related products. Treatment involves covalently bonding to the surface by means of a catalyst functional molecules each of has at least one alkoxysilane group which can form at least one first covalent bond by reaction with the oxide or hydroxide of said surface and at least one other group which can participate in free-radical polymerisation. Free-radical polymerisation from said functional molecules is then effected to build bio-compatible and/or hydrophilic polymer chains. The compatibility of the metal surface with biological material may be further improved by bonding bio-active molecules, such as heparin or heparin derived molecules to the polymer chains. Suitable metal surfaces are those of medical devices such as heat exchangers, coronary and peripheral stents and guide wires used in angioplasty. In the case of a stent, restenosis may be inhibited by incorporating into the coating a radio-labelled compound, foe example radio-labelled heparin and/or by incorporating a compound that inhibits cell proliferation e.g. mitoxantrone.

30 Claims, 19 Drawing Sheets

OTHER PUBLICATIONS

Editorial, "Biologically Active Heparin Coating in Medical Devices", The International Journal of Artificial Organs, vol. 14, No. 8, 1991, pp. 453–456.

Serruys et al. "Stenting of Coronary Arteries: Has a Modern Pandora's Box Been Opened?", New Technology; JACC; vol. 17, No. 6, May 1992, pp. 143B–154B.

Bamford and Al–Lamee "Chemical Methods for Improving the Haemocompatibility of Synthetic Polymers", Clinical Materials, 10 (1992), pp. 243–261.

Riesenfeld et al. "Surface Modification with Functionally Active Heparin", Medical Device Technology, Mar. 1995, pp. 24–31.

PCT International Search Report, PCT/GB 98/01609, Jan. 14, 1999, 3 pages.

UK Search Report, GB 9711377.3, Alan Kerry, Sep. 18, 1997, 1 page.

Clinica Article, 720/21, Sep. 2, 1996, 3 pages.

"Surface Modification of Stents for Improving Biocompatibility," Medical Device Technology (Jan./Feb. 2000).

* cited by examiner

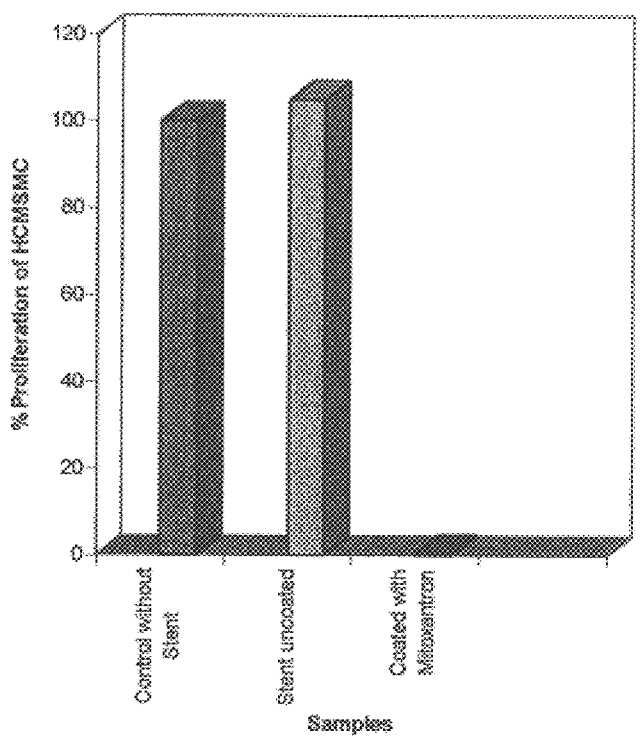
Figure 18. Inhibition of SMC proliferation in presence of untreated stent and treated with mitroxantron after 5 days incubation in the cell culture.

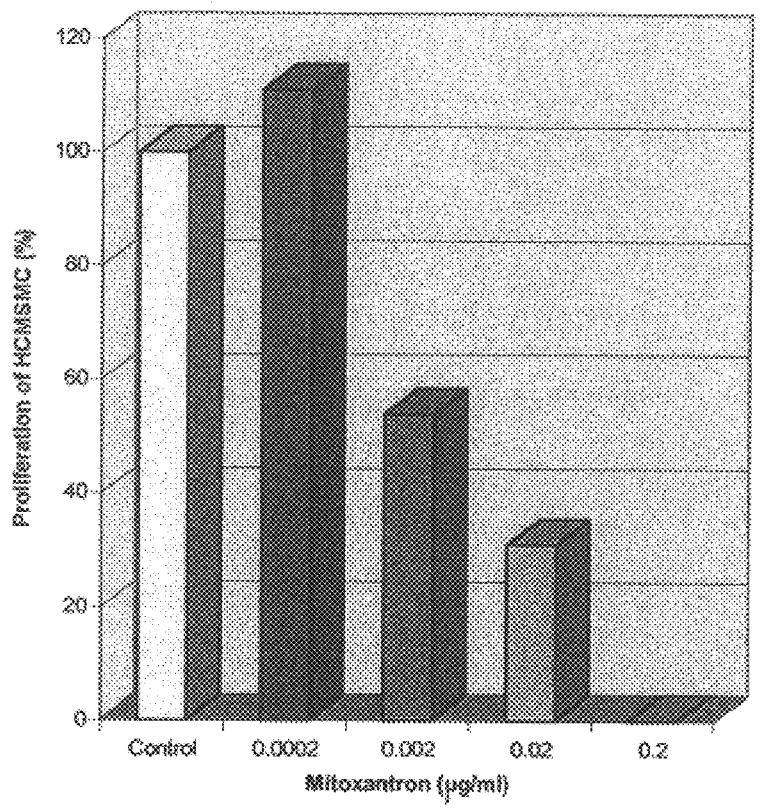
Figure 19. Inhibition of SMC proliferation at different concentrations of mitroxantron.

TREATING METAL SURFACES TO ENHANCE BIO-COMPATIBILITY AND/OR PHYSICAL CHARACTERISTICS

CROSS-REFERENCE TO RELATED APPLICATIONS

This is a continuation-in-part of International Application No. PCT/GB98/01609, which was filed on Jun. 3, 1998 and which published in English on Dec. 10, 1998, which in turn claims priority from GB 9711377.3 which was filed on Jun. 3, 1997.

FIELD OF THE INVENTION

The present invention relates to a method of treating metal surfaces to enhance the bio-compatibility and/or physical characteristics of said surfaces. The invention also relates to bio-compatible metal articles. The invention is particularly relevant to surfaces of medical devices.

BACKGROUND OF THE INVENTION

Many medical techniques are known in which human or animal blood is brought into contact with foreign surfaces, either within the body or outside the body. In some situations, usually due to mechanical characteristics, it is necessary to use metallic surfaces, as required by coronary stents (vascular endoprostheses) located within arteries or, for example, within heat exchanger assemblies external to the body. Thus, in the first application, the mechanical strength of the metal object is required whereas in the external application it is the heat transfer characteristics that are required. However, in both applications, blood or related blood products are brought into contact with metal surfaces, which may in turn have detrimental effects upon the blood itself.

The Problem of Clotting

When presented to foreign surfaces, blood has a tendency to clot. It is known that blood activation in response to contact with a foreign surface occurs by the intrinsic pathway (see FIG. 2 of Johan Riesenfeld et al, Surface Modification with Functionally Active Heparin, Medical Device Technology, March 1995 pages 24–31, the disclosure of which is incorporated herein by reference), triggered by the conversion of Hageman (F)XII to an active enzyme, FXIIa. This then initiates the sequential activation of coagulation factors FXI, FIX and FX and finally FXa converts prothrombin into enzymatically active thrombin, which precipitates the soluble plasma protein fibrinogen into a solid fibrin clot. The coagulation system is under the control of a series of regulatory mechanisms in the blood and the vascular wall, the most important being the plasma coagulation inhibitor, antithrombin (III).

Heparin is a naturally occurring substance that consists of a polysaccharide with a heterogeneous structure and a molecular weight ranging from approximately 6000 to 30000 Dalton (atomic mass units). It prevents uncontrolled clotting by suppressing the activity of the coagulation system through complexing with antithrombin (III), whose activity it powerfully enhances. Approximately one in three heparin molecules contains a sequence of highly specific structures to which antithrombin binds with high affinity. When bound to the specific sequence, the coagulation enzymes are inhibited at a rate that is several order of magnitude higher than in the absence of Heparin. Thus, the heparin molecule is not in itself an inhibitor but acts as a catalyst for natural control mechanisms without being consumed during the anticoagulation process. The catalytic nature of heparin is a desirable property for the creation of a bio-active surface, because the immobilised heparin is not functionally exhausted during exposure to blood but remains a stable active catalyst on the surface.

A method for making nonthrombogenic surfaces is disclosed in U.S. Pat. No. 3,634,123. A method for reducing thrombosis of blood, induced by contact with foreign surfaces, is shown in which the surface are treated with a cationic surface active agent and a conventional anticoagulant such as heparin. The technique disclosed in this patent is appropriate for plastic surfaces but cannot be extended to metal surfaces.

The Benestent II Group at the Department of Cardiology, University Hospital Rotterdam have developed a heparin coated Palmaz-Schatz stent, in which an end point of the heparin molecule is covalently coupled to an underlying polymer matrix, similar to the type manufactured under the trade mark Carmeda Bioactive Surface by CBAS Carmeda Inc, Sweden. The process consists of four stages:

etch the metal surface introduce a poly-amino layer which is ionically attached to the surface covalently bond the functional amino groups to the aldehyde groups of partially degraded heparin molecules chemically stabilise the bonded heparin by use of a reducing agent.

An advantage of this known approach is that it allows heparin molecules to be attached to the poly-amino layer in a relatively friendly chemical environment. However, the poly-amino layer is only physically attached to the conditioned metal surface and as such the strength of the attachment is somewhat dubious. Thus, in continuous use within the body, there is a risk of heparin or similar molecules becoming detached thereby reducing the effectiveness of the stent, which in turn may require further surgery. Similarly, in external applications, the effectiveness of the device may degrade and this degradation may be accelerated if the device has to be cleaned under particularly harsh conditions. Finally anti-coagulant coating methods generally incur relatively high manufacturing costs.

U.S. Pat. No. 5,356,433 discloses the treatment of a stent or other medical device by the alleged formation of covalent linkages between a biologically active agent and a metallic surface. In one example tantalum stents were primed with a solution in ethanol of N-(2-aminoethyl-3-aminopropyltrimethoxysilane so that a bond was formed between the tantalum oxide layer on the surface of the stents and the silicon of the silane on curing at 110° C. Heparin is then coupled to the amino groups using 1,3-ethyldimethyl-aminopropyl carbodiimide (EDC). In a second example, an ethanolic solution of an amiofunctional polymeric silane, trimethylsilylpropyl substituted polyethyleneimine is bonded to the surface of tantalum stents, also with curing at 110° C., after which heparin was coupled to the coating using EDC. Other examples use stainless steel wire, platinum tungsten wire and aminopropyl-trimethoxysilane as primer. However, priming has to be carried out with heating. The present applicants consider that covalent bonds to the metal surface are not formed under the conditions described. The reason is that the water which is inevitably present in the ethanol hydrolyses the linkages between the methoxy groups and silicon and because the reaction between the trimethoxysilane groups and surface oxide requires a catalyst which is absent. Furthermore, the heparin is coupled to the priming layer directly and not by polymeric or oligomeric spacer arms, is not sterically available, and will therefore not exhibit its full anti-coagulant activity. U.S. Pat. No. 5,607, 475 reports that the use of aminosilanes in coatings on metal or glass surfaces has not been good at producing a surface with a high level of both bio-effectiveness and stability.

U.S. Pat. No. 5,607,475 discloses an endoprosthesis having a metal surface for contact with body fluids, the metal surface having a coating thereon comprising:

(a) a silane which includes a vinyl functionality, the silane being adherent to the metal surface so that the vinyl functionality is pendant from the surface;

(b) a graft polymer, the graft polymer being covalently bonded with the pendant vinyl functionality of the adherent silane, the graft polymer being simultaneously formed and bonded to the pendant vinyl functionality by free radical reaction initiated by an oxidising metal with at least one ethylenically unsaturated monomer selected from the group consisting of acrylamide and acrylic acid;

(c) a polyamine spacer covalently attached to the graft polymer; and (d) a biomolecule covalently attached to the spacer.

The preferred primer is trichlorovinylsilane which is applied in xylene. However, under these conditions, the primer is merely physically held to the metal surface and does not form a chemical bond with oxide on the metallic surface. The procedure for subsequent attachment of heparin is lengthy and complex. The method described is neither effective nor practical, and the information and belief of the present applicants is that it has not been put into practice.

WO 97/07834 acknowledges that in order to obtain truly anti-thrombogenic surfaces, proper immobilisation of the biomolecules is the key and that the binding of a base or primer layer to metal or glass surfaces presents a problem because of the difficulty of forming covalent bonds to the surface. The priming step uses trichlorovinylsilane in xylene and therefore does not form a covalent attachment with the metal surface/ Subsequent attachment of heparin is by an elaborate multi-step procedure.

The Problem of Restenosis

Vascular restenosis is a serious complication of percutaneous transluminal coronary angioplasty (PCTA). Amongst patients who undergo this procedure, re-occlusion within 3–6 months can occur in about 35% of cases. Damage to the lining of an artery can give rise to uncontrolled proliferation of smooth cells, which gives rise to the restenosis. Intensive research has been carried out to find drugs that can avoid restenosis by inhibiting smooth cell proliferation, and stents have also been installed in an attempt to reduce the rate of restenosis.

Stents were introduced into clinical practice in 1986 in order to treat abrupt or threatened vessel closure and to prevent restenosis after angioplasty. However, when a stent is installed during angioplasty, in-stent restenosis can occur. The reasons why the arteries of some patients react to form a restenosis whereas those of others do not are not understood. Typically a patient may develop chest pain about two months after surgery, and an angiogram will reveal a blockage in the stent. Current procedures to alleviate this problem involve using a rotational device to clean out the stent, installation of a second stent within the first, and subjecting the in stent restenosis to radiotherapy. If these further procedures should fail, the patient may need to undergo by-pass surgery.

SUMMARY OF THE INVENTION

One problem with which the invention is concerned is how to provide a primer layer on a metal, glass or ceramics surface which is sufficiently durably attached that it can withstand prolonged contact with blood or other biological fluids, that enables bio-compatible hydrophilic chains or spacer arms to be grafted onto the primer layer, and that allows easy and effective attachment of heparin or other biologically active molecules.

In one aspect, the present invention provides a method of treating a metal, glass or ceramics article having at its surface oxide or hydroxide to enhance the bio-compatibility and/or physical characteristics of the surface, said method comprising the steps of:

priming said surface by means of functional molecules each of has at least one alkoxysilane group which can form at least one first covalent bond by reaction with the oxide or hydroxide of said surface and at least one other group which can participate in free-radical polymerisation, the priming being carried out by contacting said surface in an aprotic organic solvent with said functional molecules and with an acid which facilitates formation of said first covalent bond; and forming chains covalently attached to said other group of the functional molecules by free-radical graft polymerisation of at least one polymerizable monomer which imparts hydrophilic properties to said chains. The graft polymerisation is preferably a free radical polymerisation because of ease of production on a commercial scale and because of speed of the reaction. However, it could be an addition polymerisation which is ionically initiated.

In the presence of an acid, priming can be carried out under mild conditions, and thereafter formation of spacer arms and attachment of heparin or other biomolecules (if required) can be carried out under mild aqueous conditions. Attachment of heparin or other biological macromolecules may be carried out simultaneously with formation of the spacer arms, or the spacer arms may be provided with attachment sites for heparin or other biological molecules as they are formed, after which the heparin or other biological macromolecules are attached in a separate operation.

According to a second aspect of the present invention, there is provided a bio-compatible metal, glass or ceramics article a surface of which is primed with residues derived from functional molecules covalently bonded to said surface, wherein said functional molecule residues are polymers having more than one alkoxysilane group per molecule and wherein said surface carries bio-compatible hydrophilic polymer chains covalently bonded to said functional molecule residues.

A further problem with which the invention is concerned is the provision of a stent which when implanted in the human or animal body gives rise to a reduced incidence of restenosis.

That problem is solved, according to a further aspect of the invention by the provision of a stent which has a polymer coating covalently bonded to its surface, a molecular species which imparts thrombosis resistance covalently bonded in or to said coating, and a molecular species which inhibits restenosis held by ionic attraction in or to said coating.

An alternative solution to the problem provides a stent which has a polymer coating covalently bonded to its surface, wherein the coating has radio-labelling in an amount effective to inhibit restenosis.

A further solution to the above mentioned problem is to provide a stent which has a polymer coating covalently bonded to its surface, wherein the coating is radio-labelled and wherein a molecular species which inhibits restenosis is held by ionic attraction on ot to said surface, wherein the amounts of radio-labelling and of the molecular species are sufficient to inhibit restenosis.

DESCRIPTION OF PREFERRED FEATURES
Priming the Surface

Where they are monomeric, said functional molecules may be of any of the formulae:

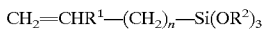
$$CH_2=CHR^1—(CH_2)_n—Si(OR^2)_3$$

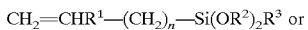
$$CH_2=CHR^1—(CH_2)_n—Si(OR^2)_2R^3 \text{ or}$$

$$CH_2=CHR^1—(CH_2)_n—Si(OR^2)R^3R^4$$

wherein $R^1$ represents a hydrogen atom or an alkyl group, $R^2$, $R^3$ and $R^4$ represent an alkyl group and n is 0 or is a positive integer. In the above molecules, preferably $R^1$ represents hydrogen, methyl or ethyl and $R^2$, $R^3$ and $R^4$ represent methyl or ethyl and the value of n is from 0 to 6. Other values of $R^3$ and $R^4$ e.g. hydroxyl or chloride are possible provided that the bond formation is not interfered with.

Preferably said vinylfunctional silane molecules are oligomers or polymers, and preferably said vinylfunctional silane molecules become bonded to said surface at a plurality of locations.

In a preferred group of oligomers or polymers, the functional molecules comprise a $[—Si—O—]_n$ chain having alkoxy groups directly attached to the silicon atoms and having olefinically unsaturated groups attached directly or via linking groups to the silicon atoms. Preferably the functional molecules have vinyl and alkoxy groups attached to the silicon atoms of the chain.

The molecules of a further preferred group of functional molecules have:
- an oligomeric or polymeric chain based on carbon atoms, which chain may also include nitrogen or oxygen atoms;
- one or more alkoxysilane or alkylalkoxysilane groups attached to the chain for forming covalent bonds with oxide or hydroxide of the surface; and
- one or more olefinically unsaturated groups which can participate in free radical polymerisation. The above functional molecules preferably have trialkoxysilane or dialkoxyalkylsilane groups, alkyl preferably being methyl or ethyl.

Particular functional molecules which may be used include one or more of:
- 3-(trimethoxysilyl) propyl methacrylate;
- vinylmethoxysiloxane oligomer;
- diethoxymethylsilyl-modified polybutadiene
- triethoxysilyl-modified polybutadiene.

Formation of Spacer Arms by Graft Polymerisation

The graft polymerisation reaction to form hydrophilic spacer arms preferably involves free-radical polymerisation including polymerising a plurality of types of polymerisable molecules to form polymer chains of said spacer arms. The polymer chains may include molecular units derived from acrylamide, and may provide sites for covalent or ionic bonding to a bio-active molecule. Such bonding sites may be provided by amino groups e.g. using as monomer or co-monomer 3-aminopropyl methacrylamide. Additionally or alternatively, the bonding sites may be carboxyl groups. A polymerizable monomer that provides sites of both type is dimethyl(methacryloyloxyethyl)(3-sulfopropyl) ammoniumbetaine (SPE) which is of formula:

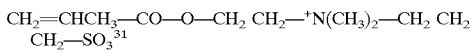
$$CH_2=CHCH_3—CO—O—CH_2\ CH_2—^+N(CH_3)_2—CH_2\ CH_2$$
$$CH_2—SO_3^{31}$$

In a further preferred embodiment, at least one type of said polymerisable molecules is suitable for additionally bonding to a bio-active molecule. In an alternative embodiment at least one of said polymerisable molecules is a modified bio-active molecule e.g. a molecule with anti-thrombolytic properties. In a further preferred embodiment, said bio-active molecule is heparin, or in the case of a modified bio-active molecule, a heparin derived molecule.

Stents and Restenosis

In a further preferred embodiment, said metal surface is a surface of a medical device, e.g. a stent. In addition to having an anti-thrombogenic compound, the stent preferably has attached thereto a compound that is effective to inhibit smooth muscle cell proliferation and restenosis. Such compounds can be covalently attached to the coating, but are preferably held by ionic bonds so that they become gradually released and are available for absorption by cells. Any physiologically acceptable at least slightly water-soluble compound that is active against smooth muscle cell proliferation and restenosis and that can form an ionic bond with the spacer arms of the covalently bonded stent coating could in principle be used. Although high molecular weight materials may be used for this purpose e.g. an anti-sense DNA fragment, simple low molecular weight compounds will be more usually employed. Amongst the classes of compound which have been reported to have appropriate properties there may be mentioned the following:

(a) Anthraquinones, e.g. the symmetrical 1,4-bis (substituted-amino)-5,8-dihydroxyanthroquinones of U.S. Pat. No. 4,197,249 and pharmaceutically acceptable salts thereof, of which mitoxantrone and its salts is preferred. See also daunorubicin, doxorubicin, and related compounds and their pharmaceutically acceptable salts.

(b) Imidazoles, e.g. chlotrimazole, miconazole, econazole and their pharmaceutically acceptable salts whose ability to inhibit proliferation of smooth muscle cells is disclosed in U.S. Pat. Nos. 5,358,959, 5,591,763 and 5,643,936.

(c) Substituted benzimidazoles and their pharmaceutically acceptable salts, e.g. as disclosed in U.S. Pat. No. 5,763,473 and EP-A-0882718.

(d) Raloxifene-type benzothiophene compounds and salts thereof, e.g as disclosed in U.S. Pat. Nos. 5,462,937, 5,457,113, 5,643,876, 5,688,796 and 5,760,030.

(e) Carbazole derivatives and their pharmaceutically acceptable salts, e.g. as disclosed in U.S. Pat. No. 5,643,939.

(f) Naphthyl compounds and their pharmaceutically acceptable salts, e.g. as disclosed in U.S. Pat. Nos. 5,484,796 and 5,691,353.

(g) Retinoids containing salt-forming groups, and pharmaceutically acceptable salts thereof, e.g. as disclosed in U.S. Pat. No. 5,798,372.

(h) Thiazoles and their pharmaceutically acceptable salts, eg as disclosed in EP-A-0928793

(i) Phenylcyclohexylcarboxamides and their pharmacologically acceptable salts, e.g. as described in U.S. Pat. No. 593,598

(j) Tranilast and its pharmaceutically acceptable salts, e.g. as described in WO 98/29104.

A further possibility for inhibiting restenosis is to incorporate radio-labelling into the stent coating e.g. by incorporating into the coating heparin labelled with $^{35}S$. A yet further possibility is both incorporate into a stent coating both a radio-labelled compoud (e.g. a compound labelled with with $^{35}S$) and a molecular species which inhibits restenosis.

BRIEF DESCRIPTION OF THE DRAWINGS

FIGS. 18 and 19 are graphs showing for various samples the percentage proliferation of human coronary media smooth muscle cells

DETAILED DESCRIPTION OF THE PREFERRED EMBODIMENTS

The invention will now be described by way of example only with reference to the previously identified drawings.

Figure 1:
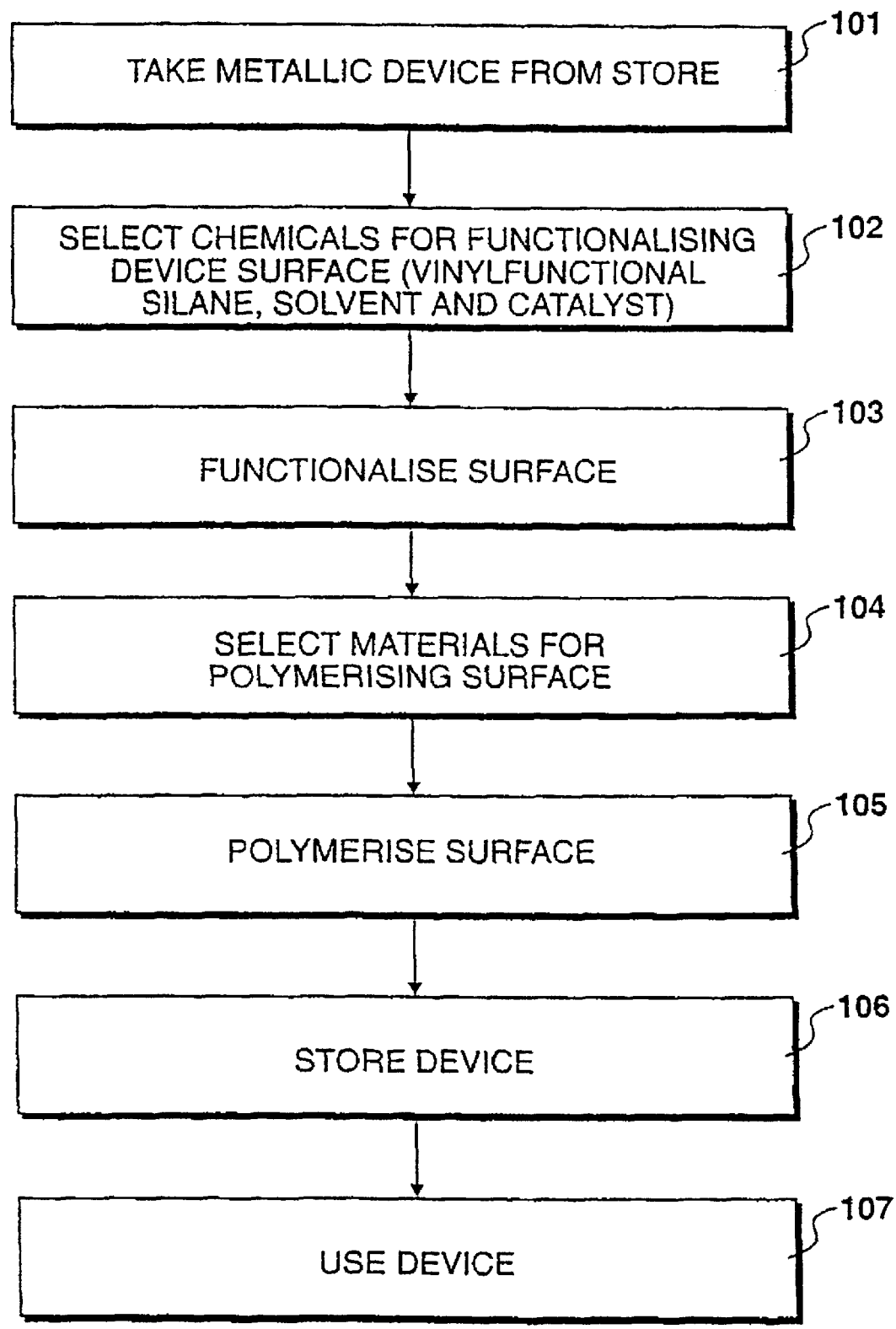
FIG. 1 shows an overview for the treatment of a metallic device including a functionalisation step and a polymerisation step.

An overview of the method of treating a metal surface to enhance its bio-compatibility with for example blood or blood related products is shown in FIG. 1. A metal surface of an article such as a medical device is particularly suitable for treating in accordance with the method shown. Typical medical devices include heat exchangers for dissipating heat in blood, coronary stents and peripheral stents (vascular endoprostheses), guide wires as used in percutaneous transluminal coronary angioplasty (PTCA), artificial heart valves and devices for storage and/or transfer of biological material such as blood or blood related products. Initially a metal article or device, is taken from store at step 101, whereafter at step 102 suitable chemicals for functionalising the device surface are selected. These chemicals include a functional molecule, a solvent and a catalyst. As indicated a suitable functional molecule is a vinylfunctional silane. At step 103 the surface of the metallic article is functionalised or primed, that is, treated with the chemicals selected at step 102. Following functionalisation, at step 104 suitable materials for polymerising on the metallic surface are selected after which polymerisation is carried out at the primed surface to form blood-compatible polymer chains, as indicated at step 105. Following polymerisation at step 105, the device with its functionalised and polymerised surface may be stored, as indicated at step 10, and subsequently used as indicated at step 107.

Figure 2:
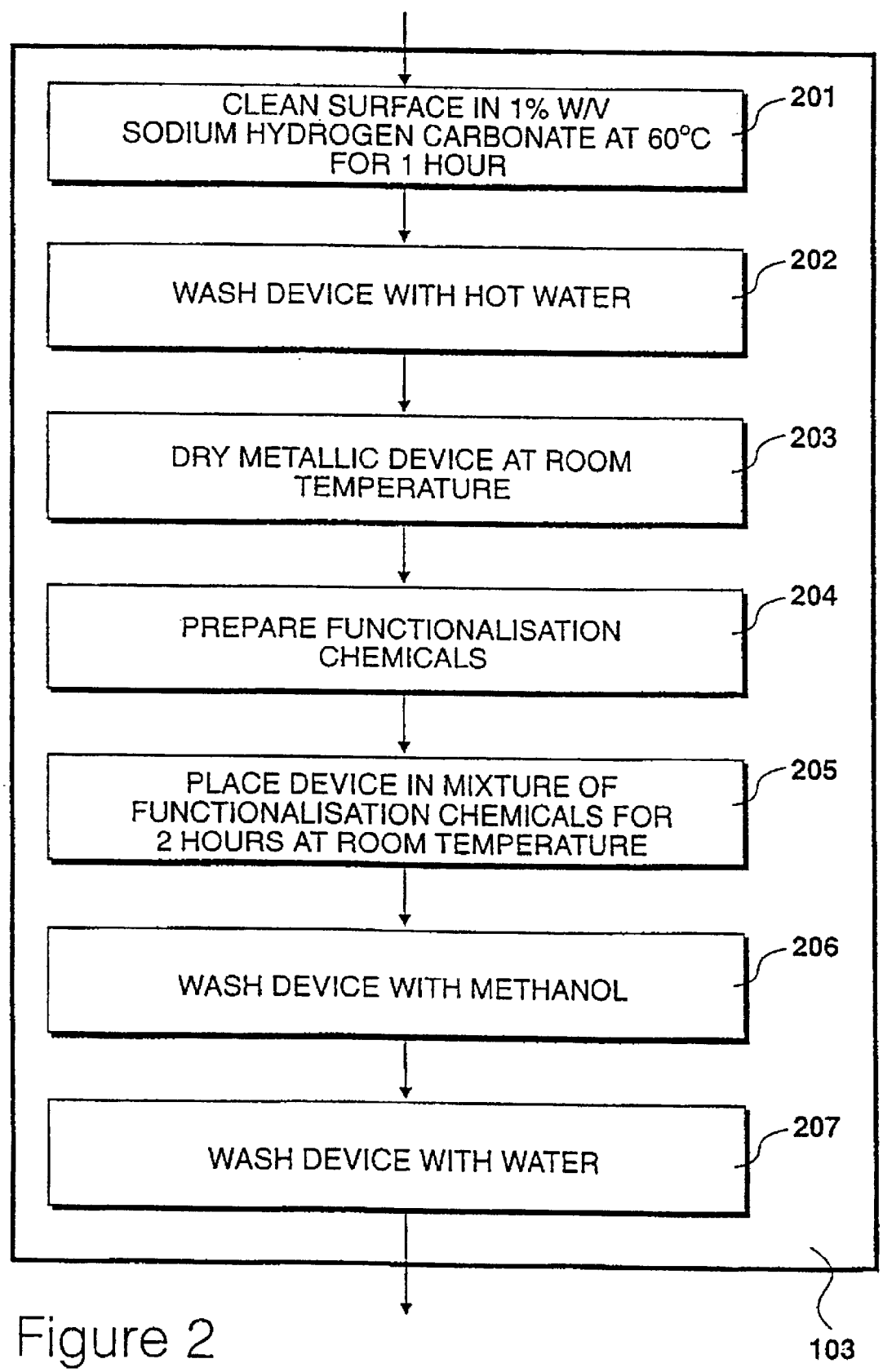
FIG. 2 details the functionalisation step identified in FIG. 1.

Step 103 for priming or functionalising a given metallic device is detailed in FIG. 2. At step 201, the surface or surfaces of a given metallic device are cleaned. For the example of a stainless steel surface, this step would typically involve placing the device in 1% w/v sodium bicarbonate solution at 60° centigrade for one hour. For other metallic surfaces, either a sodium bicarbonate solution as described or another suitable solution may be used. Furthermore for metallic devices wherein an internal surface is to be functionalised, such as for example a heat exchanger, the cleaning solution may be passed through the internal mechanism of the device, for example by pumping said solution through said device using a peristaltic pump and appropriate connection tubes. At step 202 the metallic device is washed with hot water whereafter it is dried, preferably at room temperature, as indicated at step 203. At step 204 the functionalisation chemicals selected at step 102 in FIG. 1, are prepared. The preparation involves, for example, mixing the vinylfunctional silane in a suitable solvent together with a small amount of added catalyst. Typically for stainless steel surfaces a suitable vinylfunctional silane is vinylmethoxysiloxane oligomer, a suitable solvent is toluene and a suitable catalyst is a few drops of acetic acid. At step 205 the device is placed in the prepared mixture of functionalisation chemicals for a desired length of time. In FIG. 2 the length of time is indicated as two hours and a suitable temperature is room temperature. The temperature and length of time may be varied according to the degree of functionalisation required. Thus, leaving the device in the functionalisation solution for merely one hour will provide the required functionalisation for certain applications. Similarly the temperature may be varied to effect the rate of functionalisation. At step 206 the functionalised device, having been removed from the functionalisation solution, is washed. Typically the device is washed in an organic solvent such as methanol. At step 207 the device is washed with water to remove any undesirable chemicals remaining.

Step 105 for polymerisation with bio-compatible polymer chains at a prevously primed metallic surface, may be performed in various ways. A first method for polymerising a given metallic device is detailed in FIG. 3. This step follows step 104 in FIG. 1 wherein the required polymerisation materials have been selected. At step 301 the polymerisation mixture is prepared and as indicated in this method a suitable bio-active molecule such as modified heparin is incorporated in this step. The heparin selected is a modified version in which the heparin molecules are provided with means for attachment to a polymer chain. Typically the modified heparin or other bio-active molecule, is mixed with a further polymerisaable molecule or molecules. Suitable polymerisable molecules which may be attached to the heparin are polymerisable vinyl monomers, for example acrylamide. The selected polymerisable molecules are then mixed with a small amount of free radical indicator such as sodium thiosulphate and a small amount of ammonium persulphate. Typically the mixture is used at room temperature for a period of about three hours, although it is again a matter of specific requirements regarding the exact temperature and time used. Following polymerisation at step 302, the polymerised metallic device surface is washed with water, as indicated at step 303.

Figure 4:
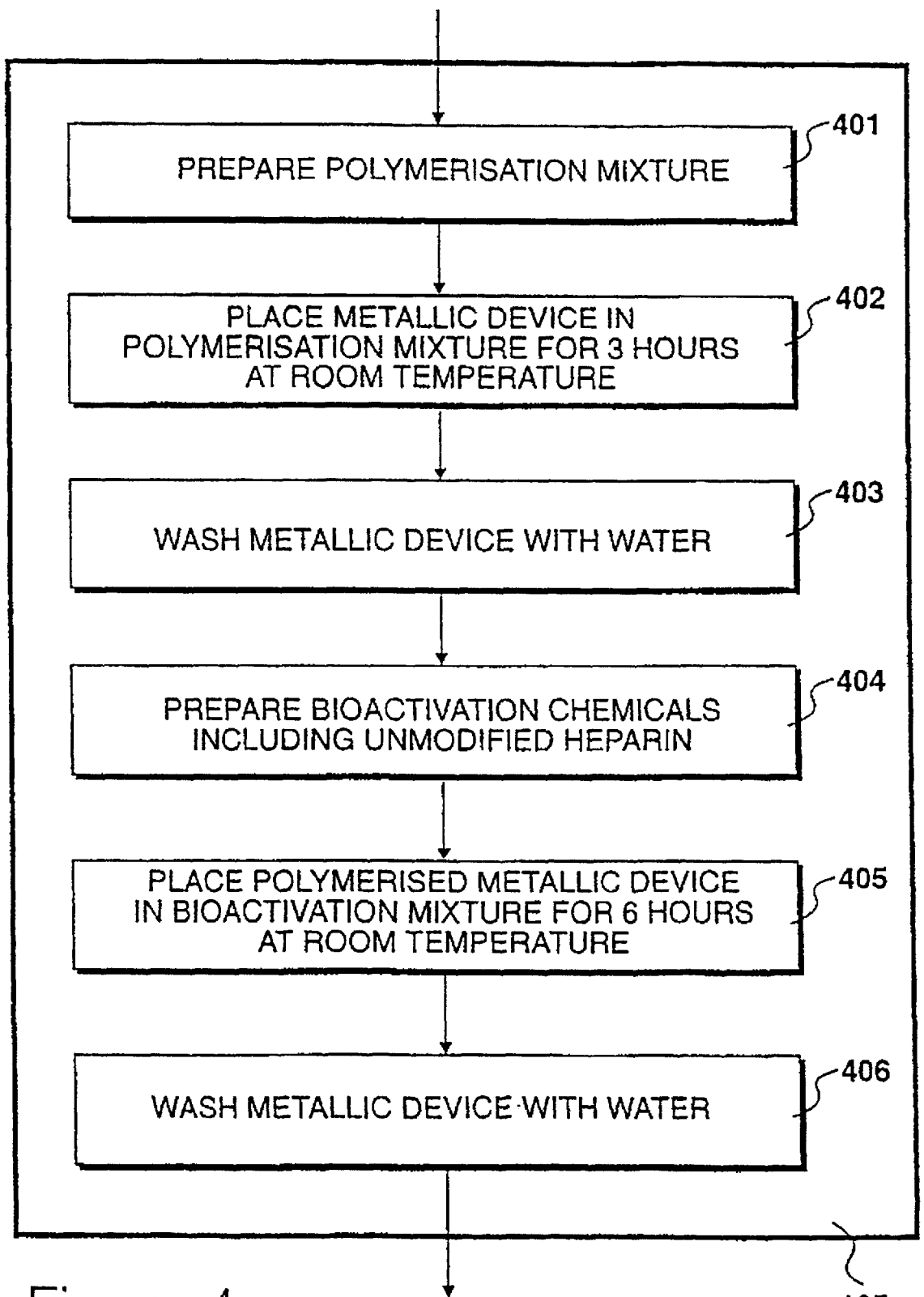
FIG. 4 details an alternative process for carrying out the polymerisation step identified in FIG. 1.

An alternative method for forming polymer at a primed surface of a metal article step 105 in FIG. 1, is detailed in FIG. 4. At step 401 a suitable polymerisable mixture is prepared. The mixture prepared at step 401 does not incorporate a bio-active molecule, and suitable polymerisable molecules are for example acrylamide and 3-aminopropyl methacrylamide prepared in an aqueous medium along with a small amount of sodium thiosulphate ($Na_2S_2O_3$) and a small amount of ammonium persulphate ($NH_4S_2O_9$). At step 402 the metallic device is treated with the prepared polymerisation mixture. The treatment conditions again may vary depending on requirements, but typically three hours at room temperature would be suitable for many medical devices. Following step 402 the metallic device is washed with water at step 403 whereafter at step 404 suitable bio-activation chemicals including for example commercially available unmodified heparin, are prepared. In the case of unmodified heparin, preparation involves dissolving the heparin n water in admixture with a suitable solvent, for example 1-ethyl-3-(-3-dimethyl amino propyl) carbodimide hydrochloride. At step 405 the polymerised metallic device is placed in the bio-activation mixture, again for a required time and at a required temperature as appropriate. Typically room temperature for a period of six hours is found to be suitable for many medical applications. Following step 405, the polymerised metallic device with incorporated bio-active molecules is washed with water, as indicated at step 406.

Figure 3:
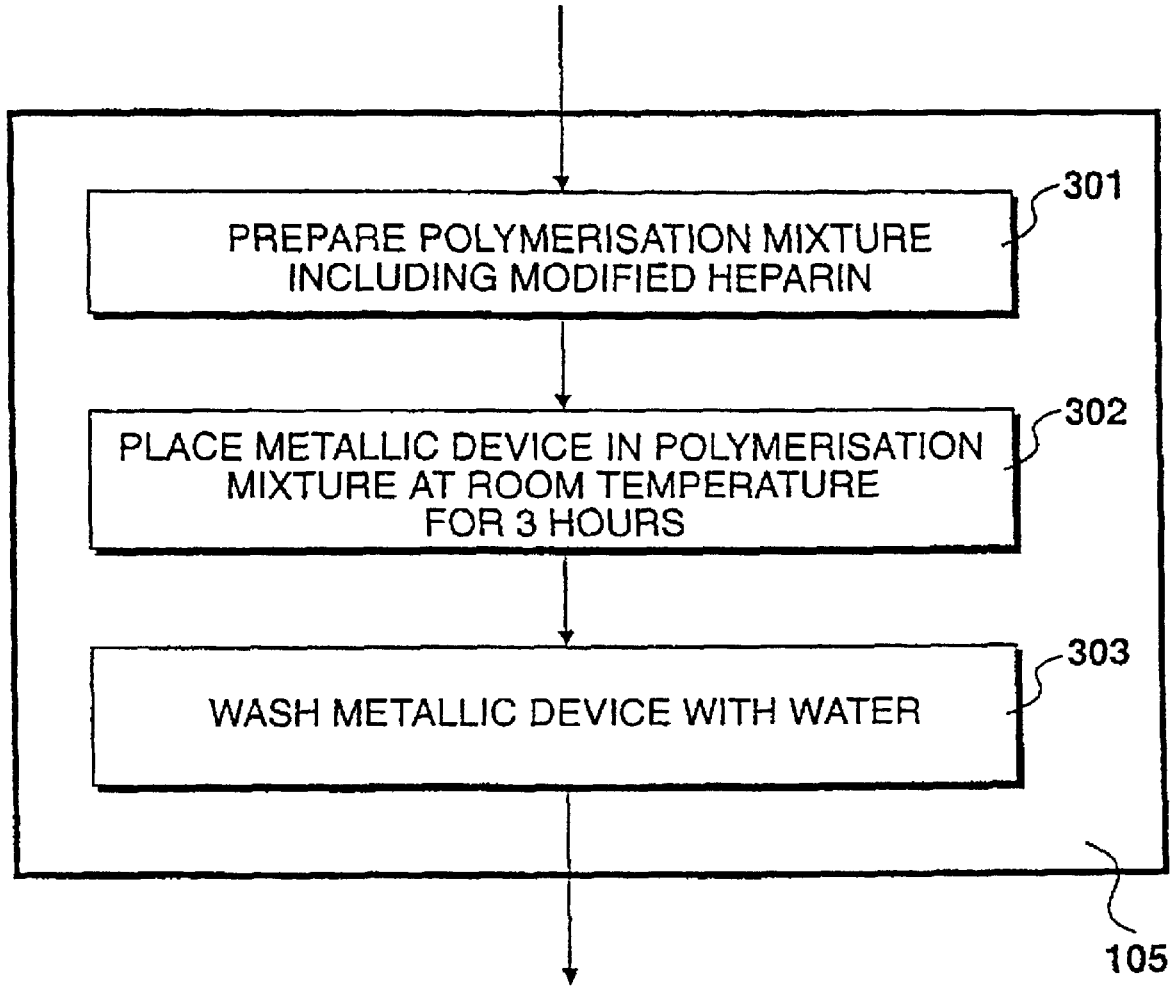
FIG. 3 details a process for performing the polymerisation step identified in FIG. 1.

The two methods of polymer formation at a primed surface of a metal article, generally illustrated in FIGS. 3 and 4 respectively, do not necessarily have to lead to incorportation of bio-active molecules. For example simple polymerisation from a functionalised metal surface, using for example acrylamide, provides hydrophilic polymer chains from said functionalised surface. In general such hydrophilic polymer chains provide a degree of improved bio-compatibility of a given metal surface with biological materials such as blood or blood related products. This is because hydrophilicity is related to lubricity of the surface and thus said surface may be physically more slippery which in itself provides an improved degree of compatibility with certain biological materials. However, incorporation of certain bio-active molecules, e.g. heparin, hirudin or prostaglandin for example, further improves the bio-compatibility (blood-compatibility) of a given metal surface. The term polymerisable molecule generally refers to a material suitable for building a given polymer chain. As indicated above one or more polymerisable molecules may be used, for example acrylamide being used alone or acrylamide being used alongside modified heparin during polymerisation or alongside a further non bio-active molecule such as 3-aminopropyl methacrylamide, which provides suitable bonding sites for incorporation of a bio-active molecule.

FIGS. 1 to 4, as described, detail two methods of treating a metal surface to enhance the bio-compatibility of said surface. Each method comprises covalently bonding functional molecules to a metal surface followed by effecting free-radical polymerisation from the functional molecules to build bio-compatible polymer chains.

Figure 5:
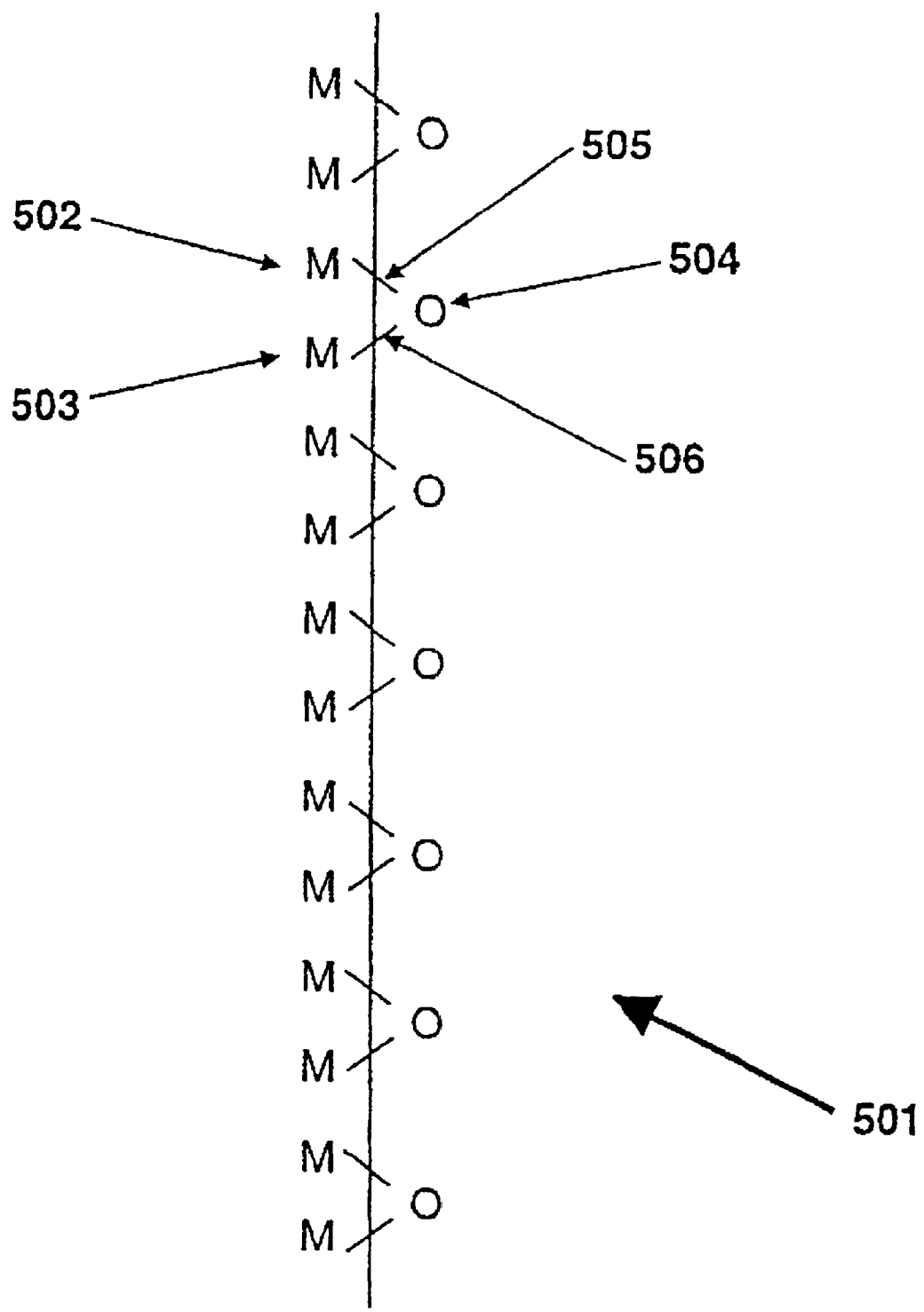
FIG. 5 illustrates a typical metal surface to be treated in accordance with the present invention.

FIG. 5 illustrates a typical surface of a metal article, 501 to be treated in accordance with the present invention. The metal surface essentially comprises an outer layer of metal atoms, 502 and 503 for example which lie below an oxide layer, said oxide layer comprising oxygen atoms such as atom 504 which are bonded to said metal atoms via bonds such as 505 and 506. The exact bonding relationship between the metal atoms and the oxygen atoms will depend on the valency of the metal atoms. Thus in the example shown the valency of said metal atoms is one, such that the electronic shells of said metal atoms are completed via a single bond to an oxygen atom for each respective metal atom.

Figure 6:
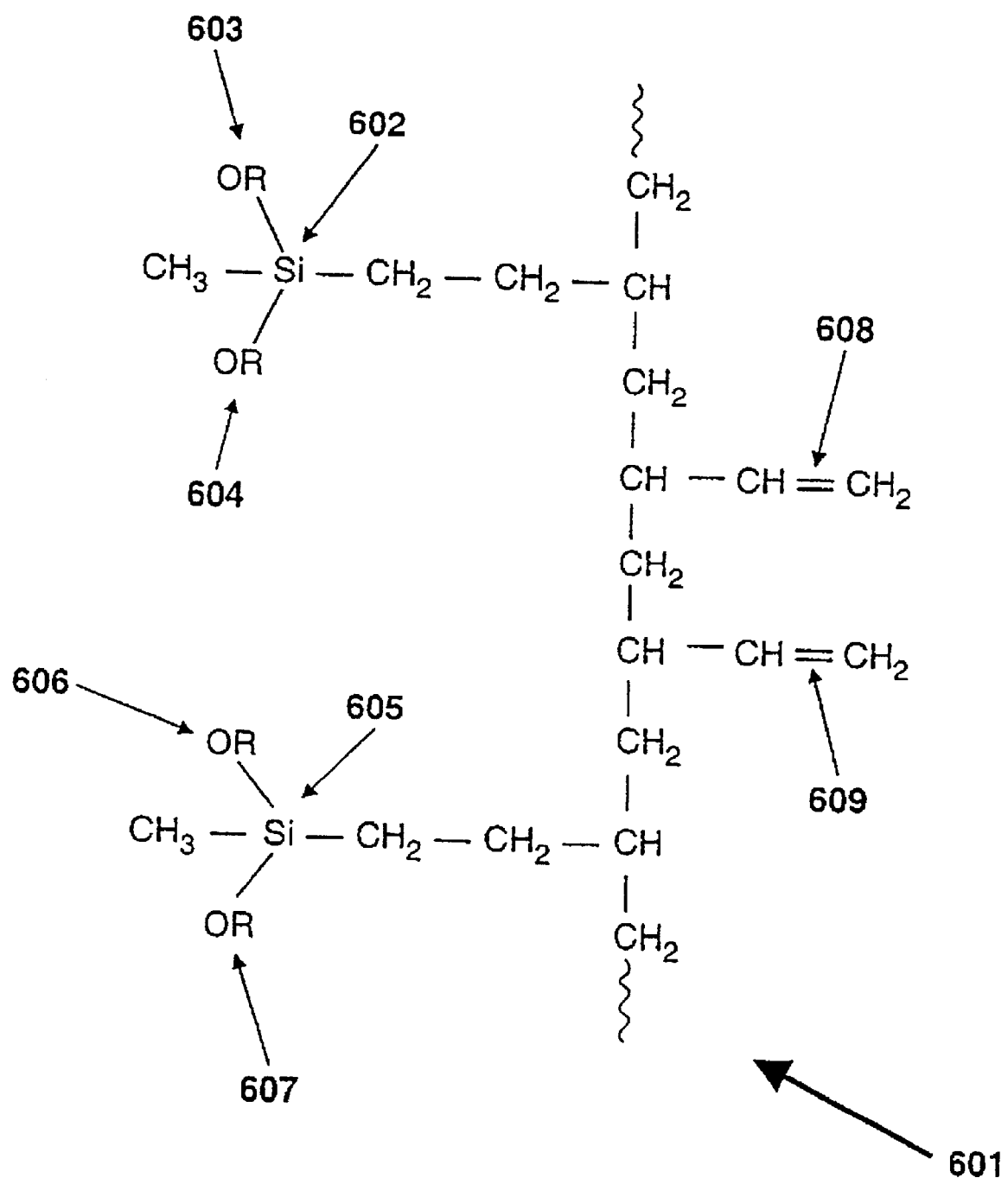
FIG. 6 details a suitable functional molecule, a vinylfunctional silane molecule, to be reacted with the metal surface illustrated in FIG. 5.

FIG. 6 details a suitable vinylfunctional silane molecule 601 to be reacted with a metal surface such as for example the metal surface illustrated in FIG. 5. As indicated at the respective ends of the vertical carbon chain on said Figure, strictly this Figure illustrates a portion or repeating unit of a silane modified polybutadiene molecule. Such materials have known uses as polymeric coating agents in for example enhancing wet electricals and use-temperature ranges for the wire and cable industry. The essential features of the vinylfunctional silane molecule illustrated are the two silicon atoms 602 and 605 and the double bonds 608 and 609. Silicon atom 602 is bonded to the two alkoxy groups 603 and 604 respectively. Similarly silicon atom 605 is bonded to alkoxyl groups 606 and 607 respectively. The alkoxy groups 603, 604, 606 and 607 each include an alkyl group R which may, for example, be a methyl group or an ethyl group. Reaction of groups 603 and 604 etc with a suitable hydrolysing agent such as acetic acid facilitates formation of bonds between silicon atoms, such as atoms 602 and 605 for example and metal surface atoms, such as atoms 502 and 503 illustrated in FIG. 5. Also pendant from the hydrocarbon chain are olefinically unsaturated groups 608 and 609 which provide sites from which graft polymerisation can take place initiated by free radicals to build bio-compatible polymer chains. A suitable vinylfunctional silane molecule is for example triethoxysilyl-modified polybutadiene as supplied by Fluorochem Limited, UK.

Figure 7:
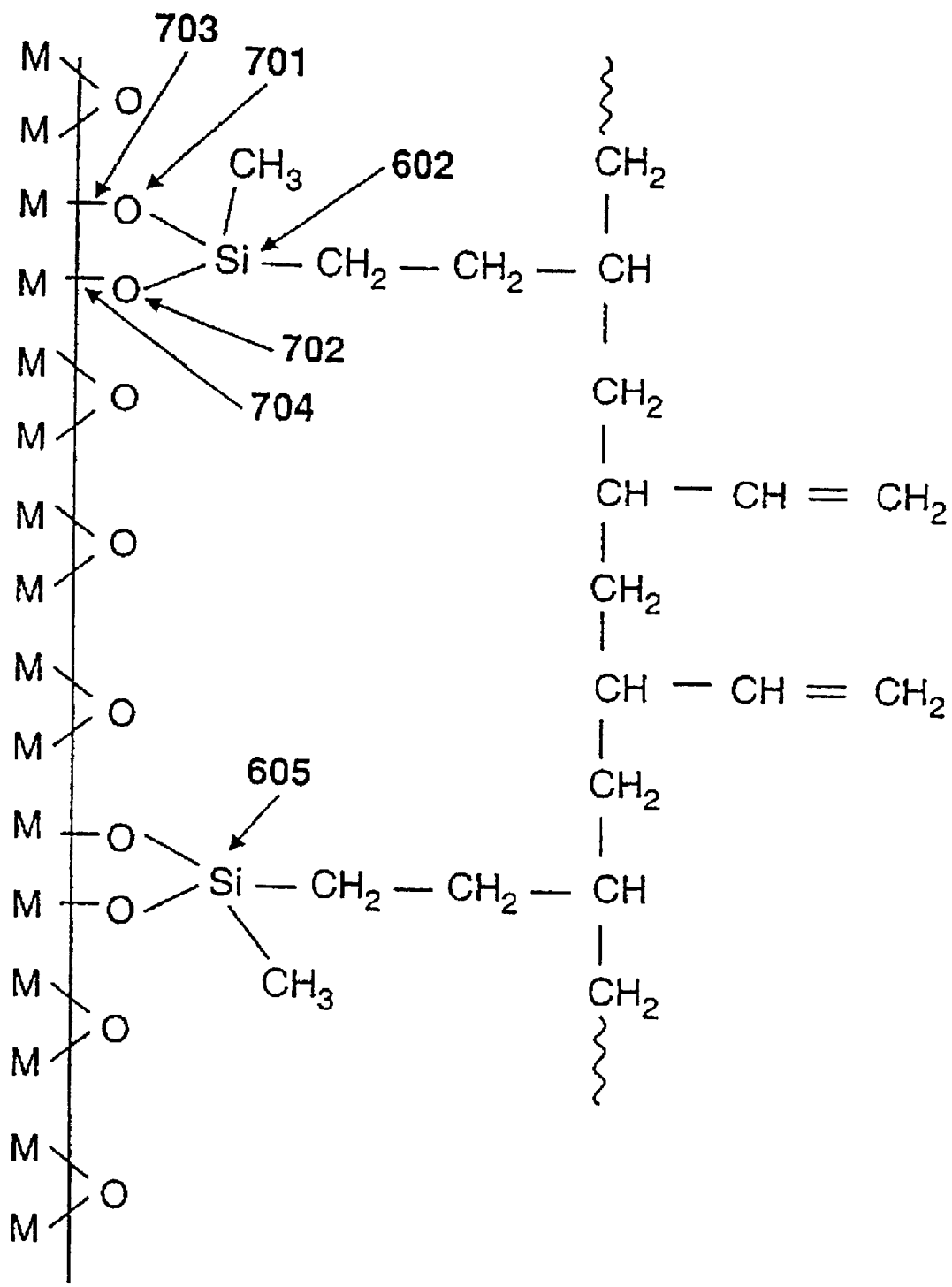
FIG. 7 illustrates the silane molecule detailed in FIG. 6 covalently bonded to the metal surface illustrated in FIG. 5.

FIG. 7 illustrates covalent attachment of the silane molecule detailed in FIG. 6 to the metal surface illustrated in FIG. 5. The illustration diagramatically shows silicon atoms 602 and 605 connected to metal via oxygen 701 and 702 via covalent bonds 703 and 704. The illustration shows two covalent bonds attaching each silicon atom to the surface which is preferable for strength and reliability of attachment. However it may be that in some cases a given silicon atom is attached by a single covalent linkage via an oxygen atom to a given metal atom in which case the other bonding site associated with said silicon atom could, for example, be taken up by a hydrogen atom.

The molecule illustrated in FIG. 6 is a polymer. Since polymers consist of repeating units all such units or a single unit or several may be bonded to said surface, thus providing covalent bonding to a metal surface at a plurality of locations. Also the particular molecule illustrated is seen to have a pair of silicon atoms in a repeating unit and thus in this case a plurality of sites are available for a given repeating unit to bond to a metal surface.

The reaction of a vinylfunctional polymer silane with a metallic surface is facilitated (catalysed) by hydrogen ions, as for example supplied from a weak acid such as acetic acid. The reaction is performed in a solvent such as a hydrocarbon solvent e.g. toluene or cyclohexane, since too much water is not suitable for this reaction, water interfering with the desired reaction in that it hydrolyses the "OR" groups, such as groups 603 and 604 in FIG. 6.

Figure 8:
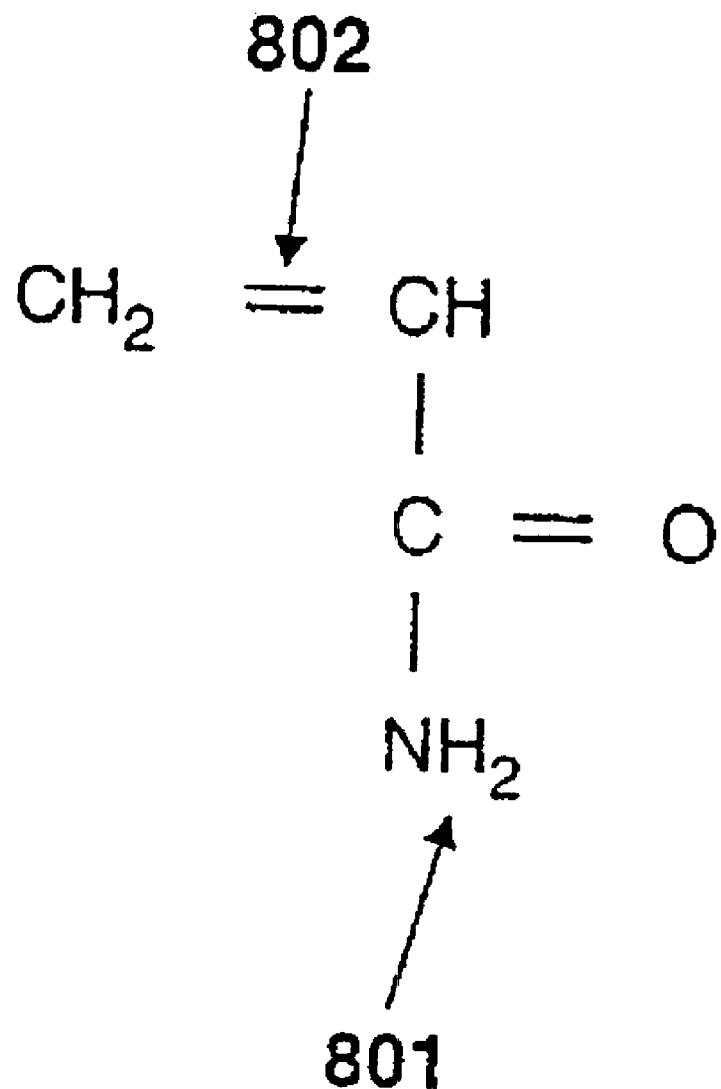
FIG. 8 details a suitable vinyl monomer for free radical polymerisation, said monomer being acrylamide.

FIG. 8 details a suitable polymerisable molecule (vinyl monomer) used to substantially build a polymer chain from the double bonds 608 and 609 shown in FIG. 6. The molecule shown is acrylamide and it has an amide group 801 and a double bond 802 which can be used for free-radical polymerisation of these molecules from vinylfunctional silane molecules covalently bonded to a metal surface. Such a polymerisable monomer is preferably water soluble, but this solubility is not essential since strictly it depends on the solvents used in the polymerisation reactions and vice versa.

Figure 9:
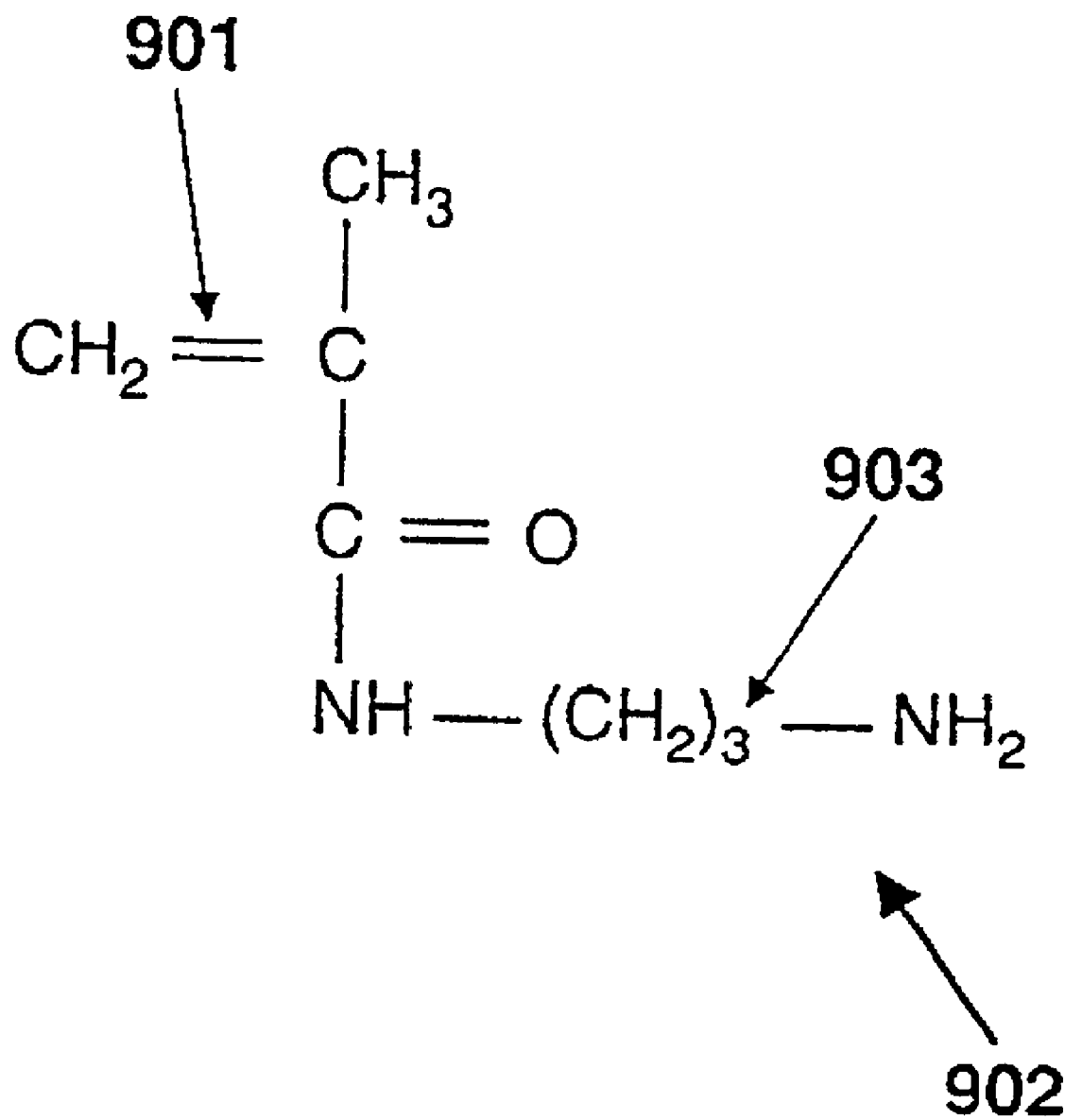
FIG. 9 details a second vinyl monomer suitable for bonding to a bio-active molecule, said monomer being known as 3-aminopropyl methacrylamide.

FIG. 9 details a second polymerisable monomer known as 3-aminopropyl methacrylamide which can build a polymer chain in conjunction with the molecule shown in FIG. 8. Free radical olymerisation occurs through the double bond 901, and amine group 902 attached to carbon chain 903 provides a site for additional bonding of a bio-active molecule such as heparin. The carbon chain 903 is seen to consist of three carbon atoms, but other lengths may be suitable and preferable for particular applications.

Figure 10:
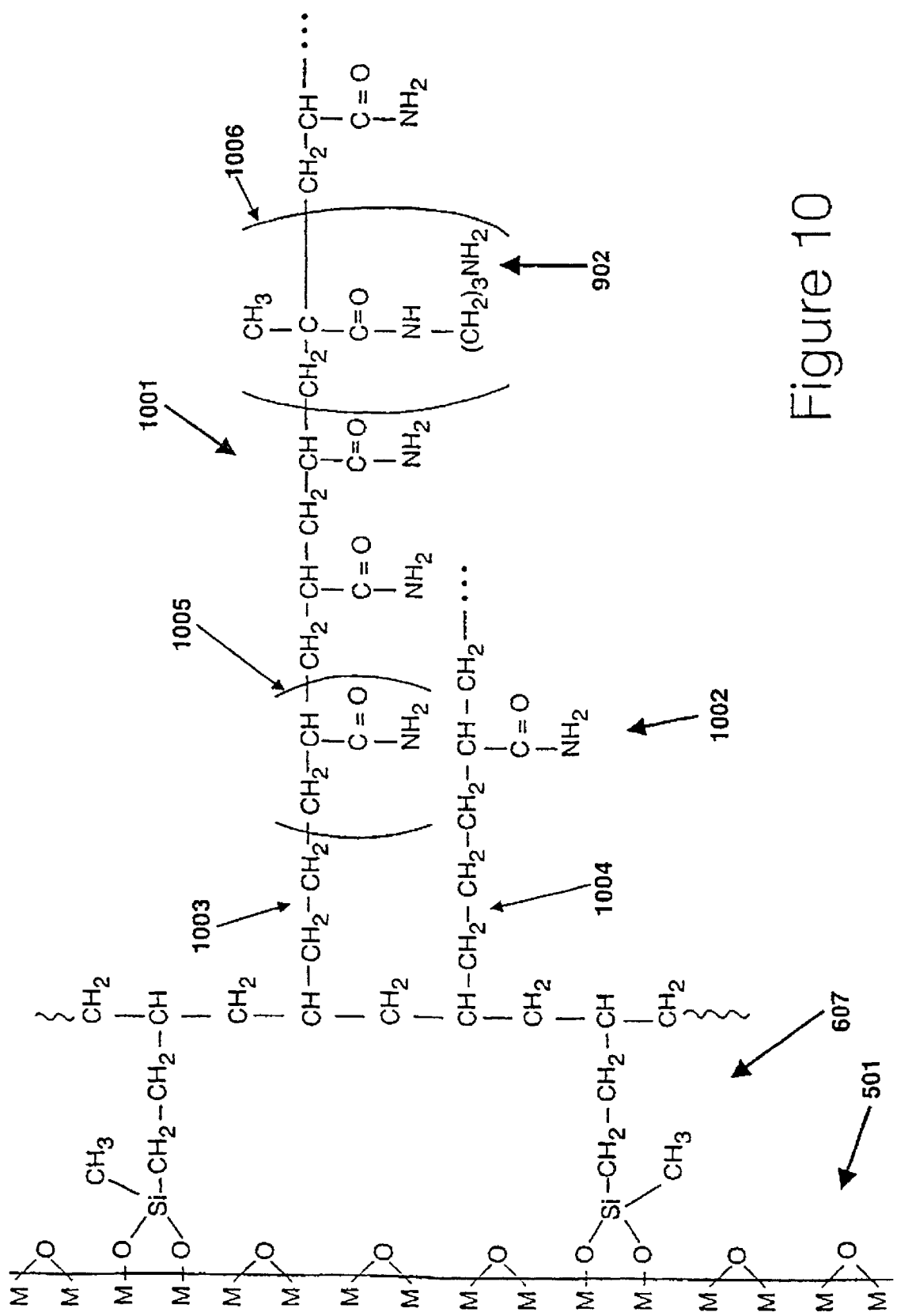
FIG. 10 details the chemical structure, following polymerisation, of the functionalised metallic surface shown in FIG. 7, wherein polymerisation has been effected using acrylamide detailed in FIG. 8 and 3-aminopropyl methacrylamide detailed in FIG. 9.

FIG. 10 shows polymerisation at a previously primed metallic surface in accordance with the steps detailed in FIG. 4 using the polymerisaable molecules detailed in FIGS. 8 and 9. Polymer chains 1001 and 1002 are seen to be covalently attached to a vinylfunctional silane molecule by covalent bonds 1003 and 1004 respectively. The portion of chain 1001 in braces 1005 is a molecular unit, resulting from incorporation of an acrylamide monomer and in braces 1006 is a portion of the polymer chain resulting from incorporation of a 3-aminopropyl methacrylamide monomer. Chains 1001 and 1002 are substantially similar in that they mainly consist of molecular units of the type in braces 1005, with occasional units of the type in braces 1006. The placement of the 3-aminopropyl methacrylamide derived molecular units is random and thus polymer chains 1001 and 1002 will not be identical in this respect. Similarly free-radical polymerisation is itself of a random nature and thus polymer chains 1001 and 1002 are likely to have different lengths. The relative proportions of the polymerisable molecules used may be varied to allow some control over how many portions of a given polymer chain are represented by the molecular unit suitable for attachment of a bio-active molecule. This is important in that when it comes to attachment of a bio-active molecule it may be desirable to minimise the amount of bio-active molecule used. Such minimisation is determined by various factors, one being the number of suitable attachment sites available. On the other hand it may be desirable to maximise the number of sites available for attachment of a bio-active molecule, such as heparin, and thus the relative proportions of the polymerisable molecules may be set to facilitate this. The major factor governing the individual proportions of selected polymerisable molecules is the rate of reaction associated with a given molecule relative to the other polymerisable molecule or molecules. Control over the proportions of the particular polymerisable molecules (one possibly being a bio-active molecule) is particularly important when the process is scaled up in a manufacturing environment where costs of individual chemicals and bio-chemicals used become an important commercial concern.

Figure 11:
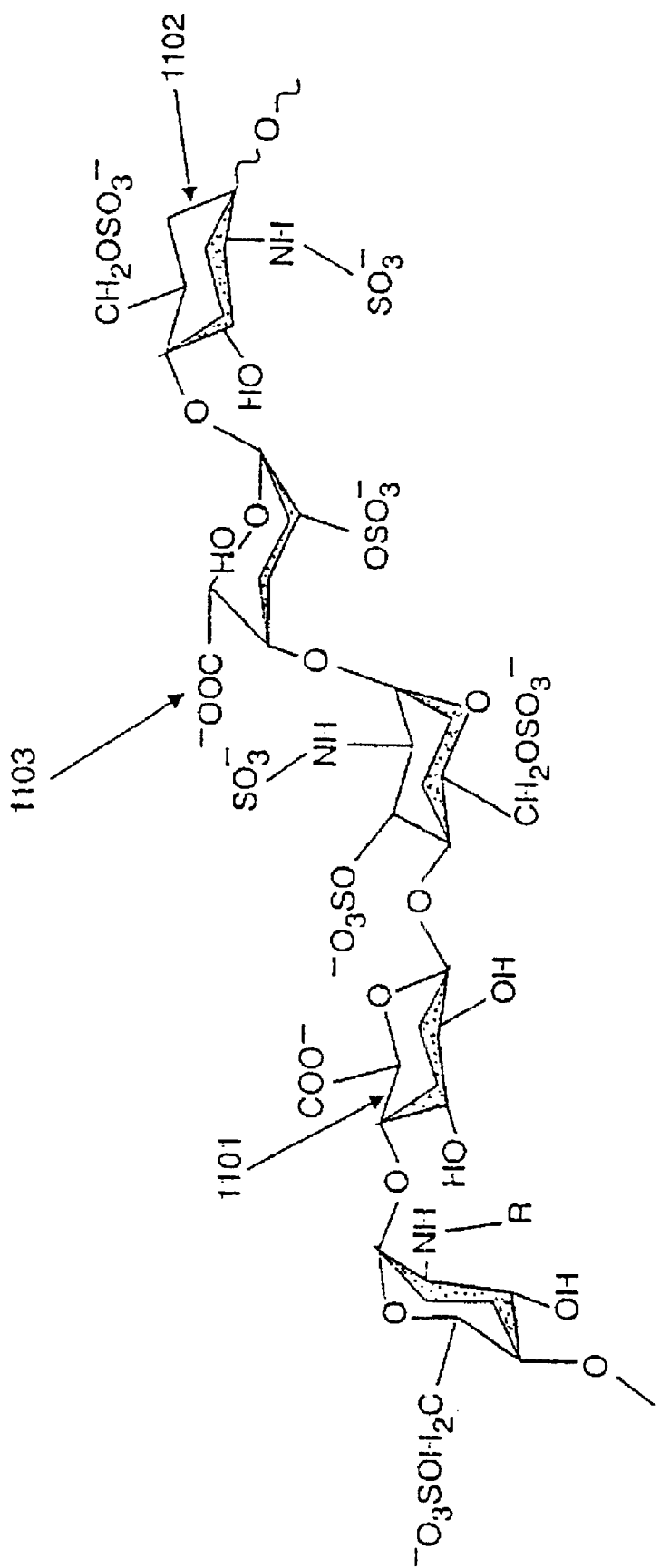
FIG. 11 details the chemical structure of a repeating unit of a heparin molecule, said molecule being desirable so as to further enhance blood-compatibility of the polymer chains shown in FIG. 10.

FIG. 11 details the chemical structure of a repeating unit of heparin which is a preferred bio-active molecule for incorporation into or bonding to the polymer chains shown in FIG. 10. The repeating unit of this molecule essentially consists of five connected monosaccharide rings such as for example rings 1101 and 1102. The carboxy group 1103 provides means for attachment to certain polymer chains such as chains 1001 and 1002 shown in FIG. 10. Specifically carboxy group 1003 covalently bonds to the amine group associated with polymer chain portions such as the molecular unit in braces 1006 in FIG. 10.

Figure 12:
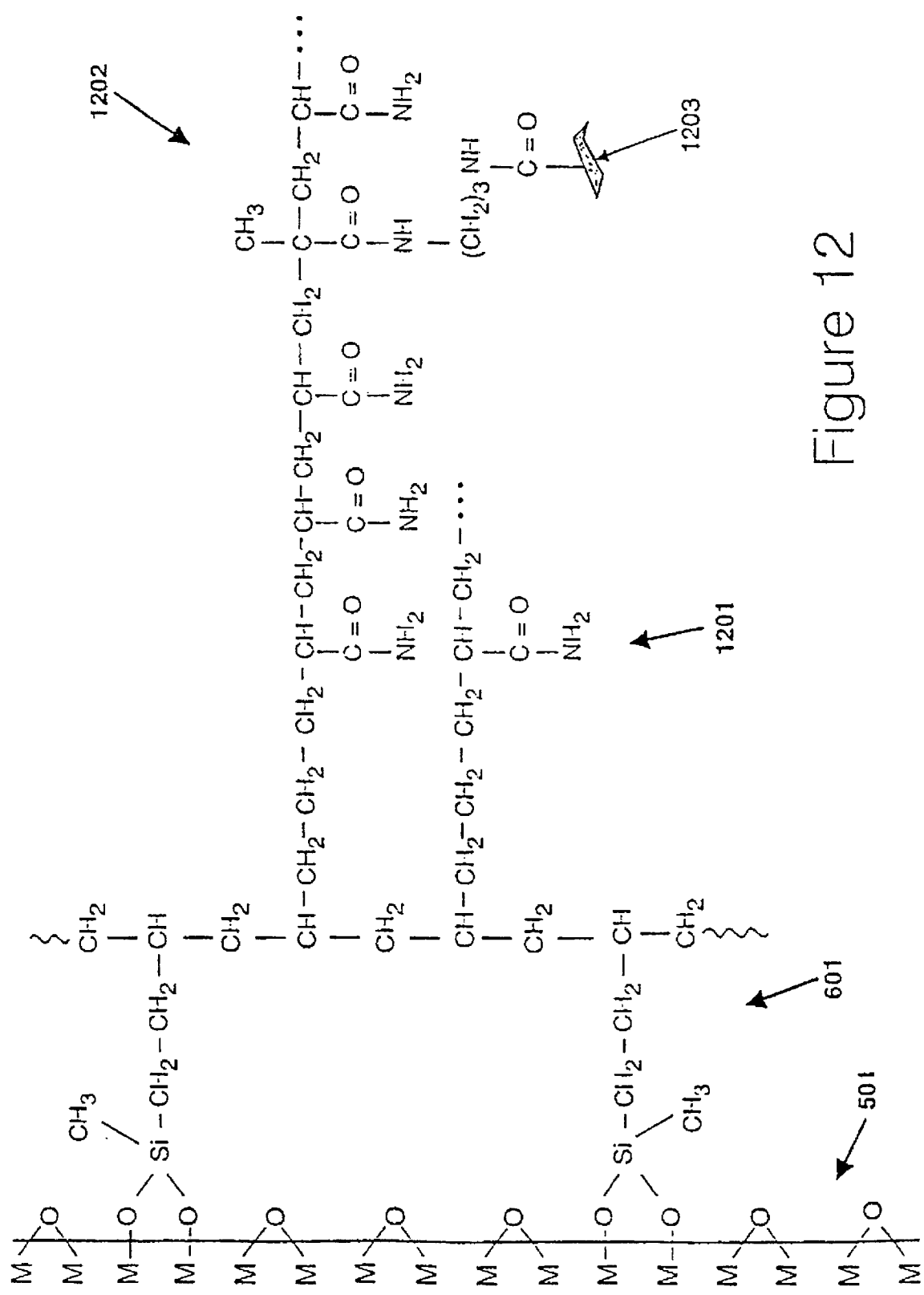
FIG. 12 details a metallic surface such as shown in FIG. 10, wherein said surface has been further treated with heparin.

FIG. 12 illustrates diagrammatically a portion of a metallic surface, functionalised with a covalently bonded vinylfunctional polymeric silane, wherein polymerisation has effected formation of blood-compatible polymer chains in accordance with the steps outlined in FIG. 4 and wherein at step 405, incorporation of a bio-active molecule has been effected. In FIG. 12 the blood-compatible polymer chains, 1201 and 1202, incorporate heparin molecules, detailed in FIG. 11, such as molecule 1203, at various positions along the polymer chains. It should be noted that the Figures in general illustrate the general principles involved, and thus for example in FIG. 12 the molecule 1203, as illustrated, is not representative of the size of the molecule involved, a typical heparin molecule being extremely large compared with an acrylamide monomer for example.

Figure 13:
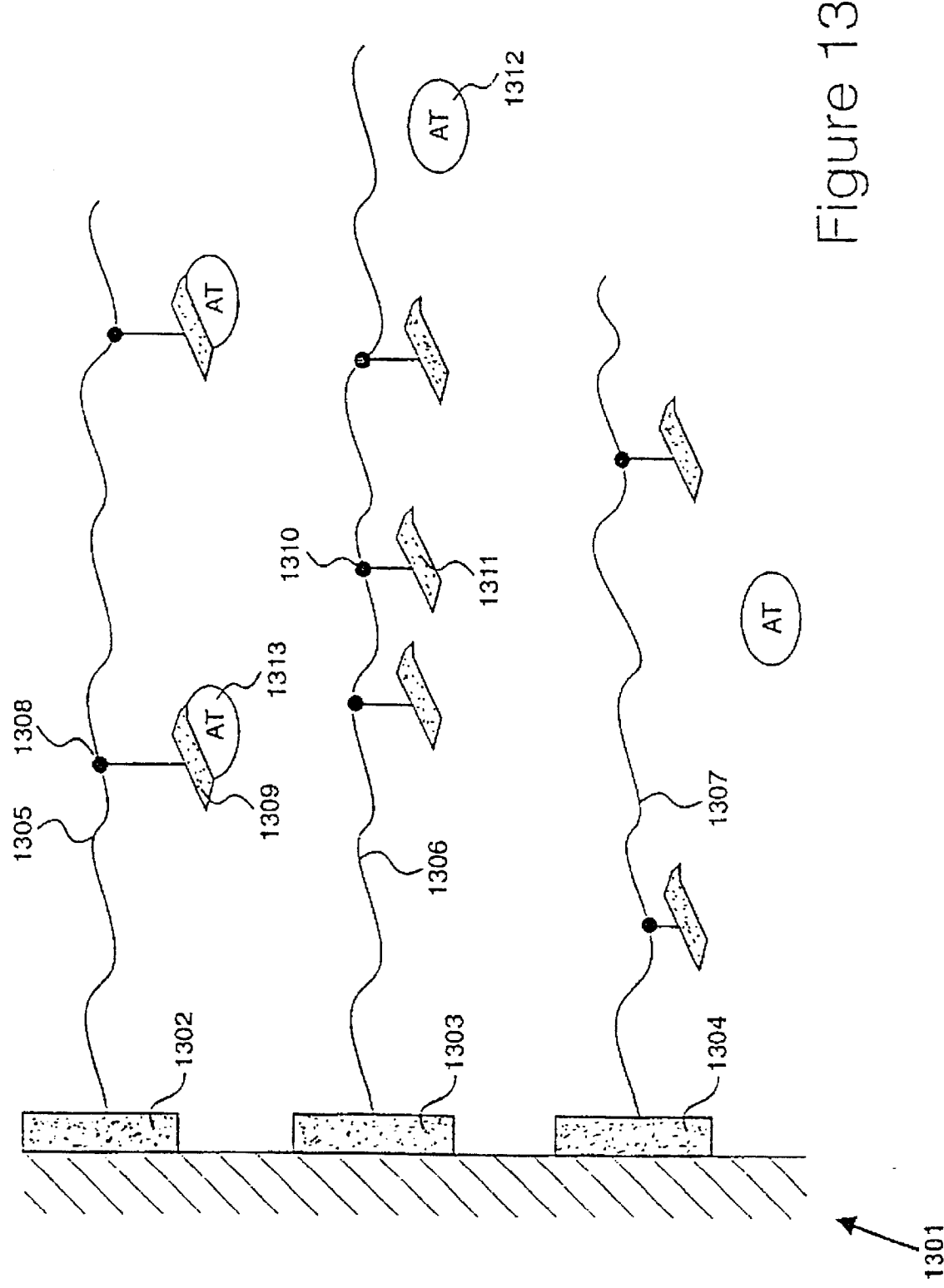
FIG. 13 generally illustrates a metallic surface with polymer chains as detailed in FIG. 12, interacting with antithrombin (III).

The functionalised and polymerised metal surface detailed in FIG. 12 is more generally illustrated in FIG. 13 wherein metal surface 1301 is preferably a surface of a medical device, said device being used in conjunction with biological material such as blood or blood related products. The surface 1301 has been functionalised by covalently bonding vinylfunctional silane molecules 1302, 1303 and 1304 respectively to said surface. Each respective said vinylfunctional silane molecule is bonded to a polymer chain 1305, 1306 and 1307 respectively, said polymer chains having been built from said vinylfunctional silane molecules via free-radical polymerisation, in accordance with the method illustrated in FIG. 4. Certain portions of the chains such as molecular units 1308 and 1310 provide for attachment of bio-active molecules such as heparin molecules 1309 and 1311 respectively. Thus molecular units 1308 and 1310 (detailed in FIG. 10 in braces 1006) are attached to a heparin molecule via a bond formed between the amine group 902 shown in FIG. 10 and the carboxy group 1103 shown in FIG. 11. For illustrative purposes, only one polymer chain such as chain 1305 is shown emanating from any given vinylfunctional silane molecule, such as molecule 1302. In reality many such chains will be emanating from a given vinylfunctional silane molecule, in particular if said molecule is a vinylfunctional polymeric silane as is the case in the preferred embodiment. Furthermore silane molecules of the type detailed in FIG. 10 are seen to provide two polymer chains per repeating unit of the polymeric silane. FIG. 13 also shows molecules of antithrombin (III), such as the free molecule 1312 and molecule 1313, the latter which is illustrated interacting with heparin molecule 1309.

Figure 14:
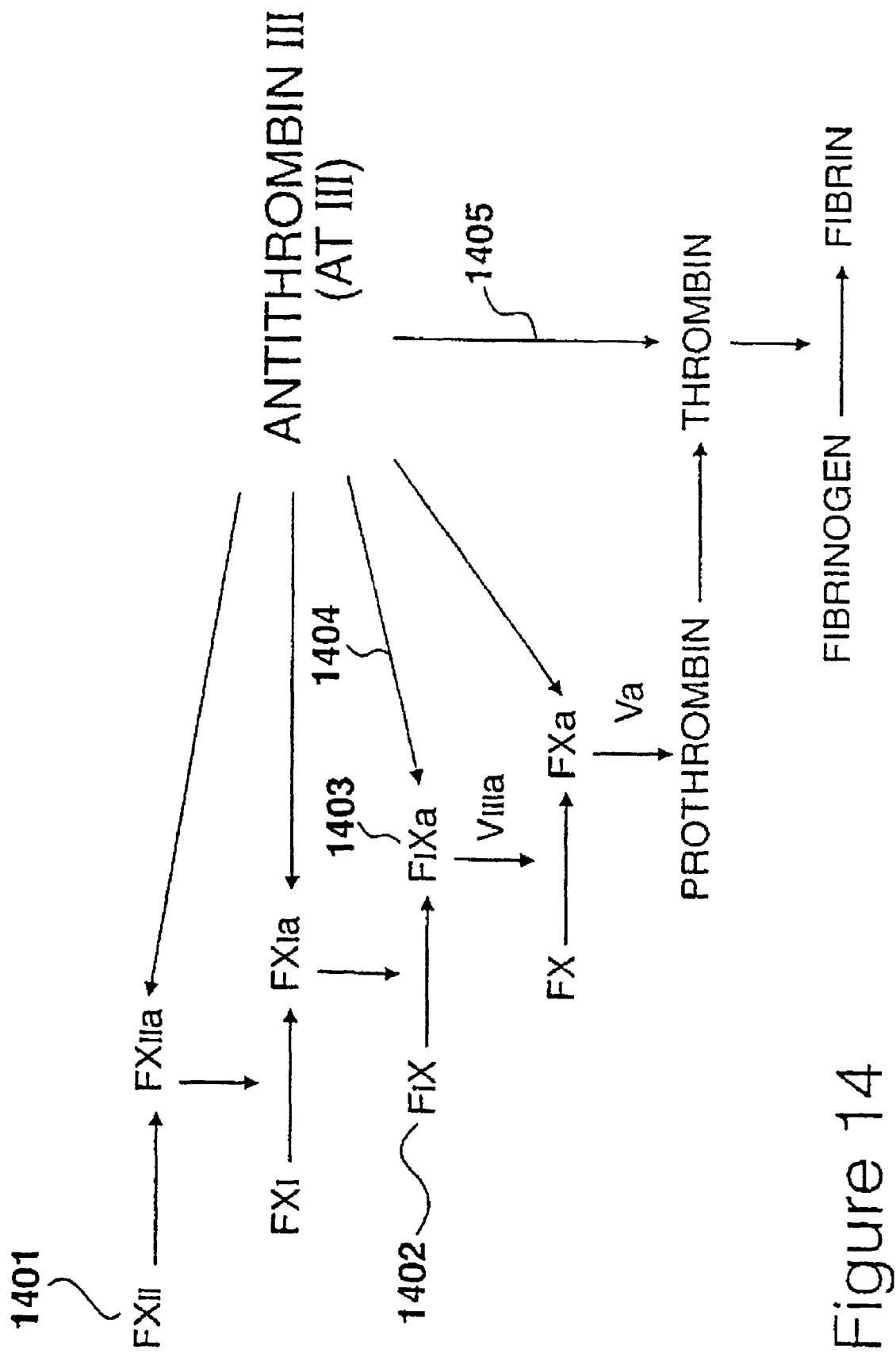
FIG. 14 details the interaction of antithrombin (III) with blood clotting factors so as to prevent formation of fibrin and hence blood clots.

The interaction of antithrombin (III) with blood has been mentioned in the introduction, but further details are provided in FIG. 14. The mechanism for the formation of fibrin is complex and involves the sequential activation of coagulation factors such as factor 1401 and 1402 for example. Antithrombin (III) is able to inhibit the sequential mechanism at various points in the reaction sequence. Thus antithrombin (III) may directly inhibit the formation of factor 1403 as indicated by inhibiting process (arrow) 1404. Similarly antithrombin (III) may directly inhibit the conversion of prothrombin to thrombin as indicated by inhibiting process 1405. Thus, the ability of a metallic surface to facilitate and enhance the interaction of antithrombin (III) with said factors is seen to be highly desirable. Use of heparin molecules in accordance with the present invention, generally indicated in FIG. 13 is believed to improve the blood-compatibility of a given metal surface through complex formation between covalently bound heparin on said surface and antithrombin (III).

Figure 15:
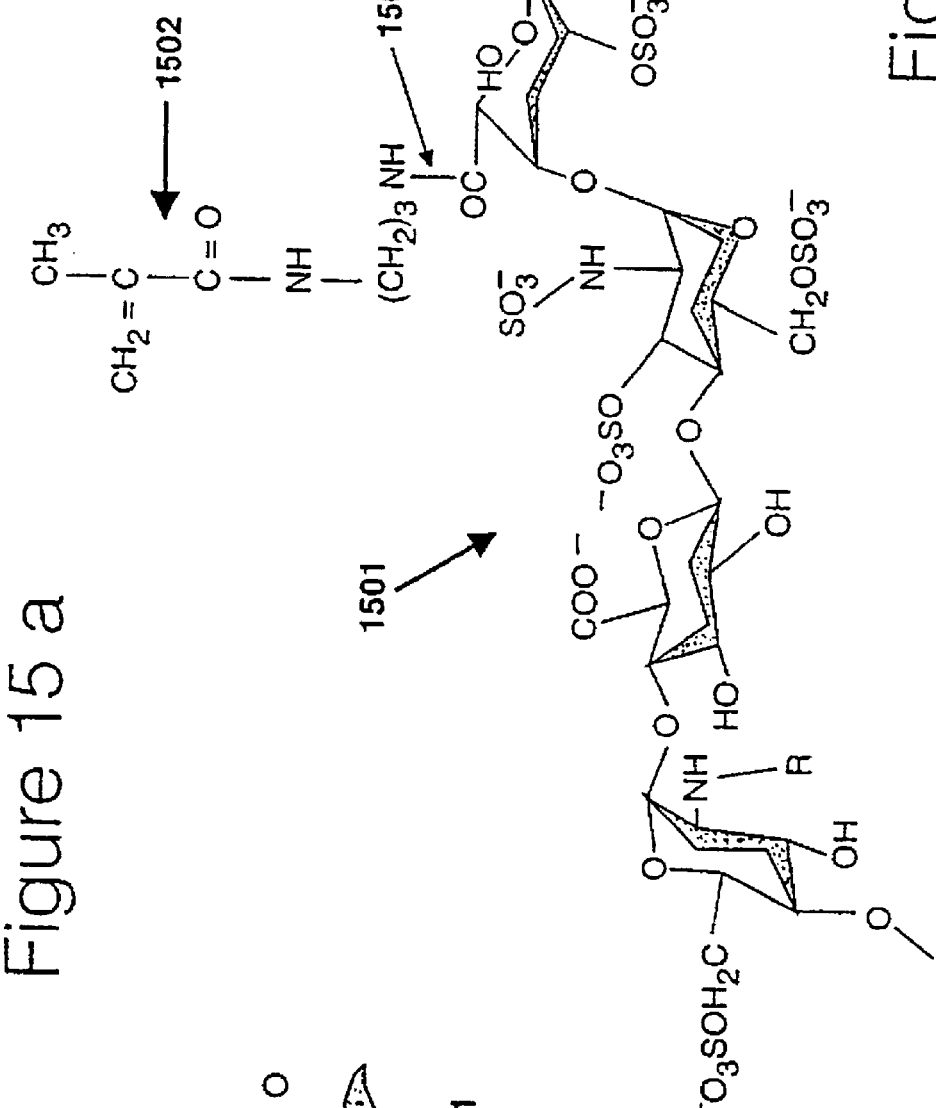
FIG. 15(a) details a molecule of modified heparin.
FIG. 15(b) further details the molecule shown in FIG. 15(a), which may be reacted in conjunction with a vinyl monomer such as shown in FIG. 8, with a functionalised surface such as shown in FIG. 7, to produce substantially the polymerised surface shown in FIG. 12.
Figure 15:
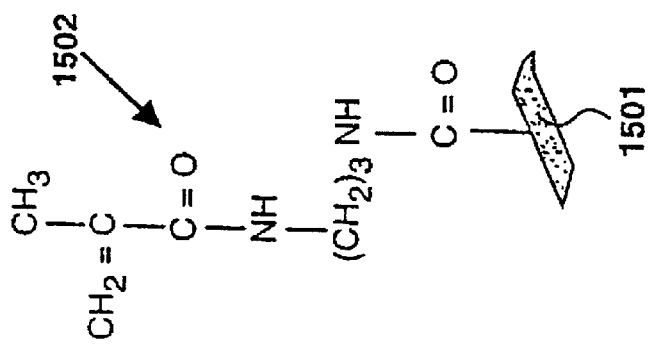

Polymerisation at a metal surface in accordance with the alternative method indicated in FIG. 3 is performed using a modified bio-molecule such as heparin macromer. A suitable heparin macromer may be produced in accordance with a method devised by co-inventor K. G. Al-Lamee. This earlier disclosed method is published in the journal "Clinical Materials 10 (1992)", under the title "*Chemical Methods for Improving the Haemocompatibility of Synthetic Polymers*". FIG. 15(*a*) details a modified heparin molecule, produced in accordance with this earlier disclosed method, wherein a heparin molecule 1501 has been modified by covalently bonding to an amine molecule, said amine molecule substantially forming the chemical chain 1502. The covalent bonding between heparin molecule 1501 and chemical chain 1502 is further detailed in FIG. 15(*b*) wherein the relevant covalent bond 1503 is seen to be between a carbon atom on the heparin molecule 1501 and a nitrogen atom on chemical chain 1502.

The molecule of modified heparin illustrated in FIG. 15(*b*) is seen to be a portion, or repeating unit, of a polymer chain. This modified bio-active molecule may be reacted in conjunction with a vinyl monomer such as acrylamide in the presence of a functionalised metallic surface, to produce substantially the polymerised surface shown in FIG. 12. The molecule illustrated in FIG. 15(*b*) produces polymer chains which are identical to those produced by the method of FIG. 3. A functionalised and polymerised metallic surface produced using modified heparin molecules provides a metal surface with substantially the same functionality with regards to blood-compatibility as with the former method using unmodified heparin, said functionality generally being illustrated in FIG. 13.

Both of the above described methods for incorporation of heparin onto the surface of a metal could alternatively be applied to other suitable anticoagulants or any other suitable drugs as may be required. Thus, for example, prostaglandin (an anti-platelet agent) or hirudin may be incorporated by similar methods. In the case of heparin, amine groups are necessary to effect suitable bonding, either to a polymer chain already bonded to a given metal surface or to form a suitable modified heparin molecule for incorporation in free-radical polymerisation. In the case of hirudin a carboxyl group, rather than an amine group, is required. Similarly, drugs containing carboxyl groups may be bonded, in accordance with the above methods, via compounds having suitable hydroxyl groups.

Figure 16:
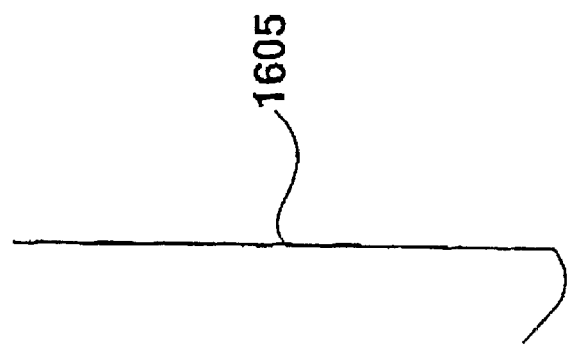
FIGS. 16(a) to 16(c) show typical metal medical devices that may be treated in accordance with the present invention.
Figure 16:
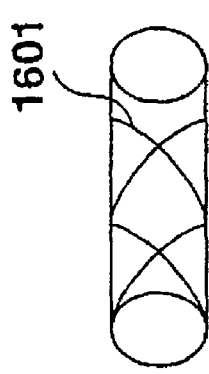
Figure 16:
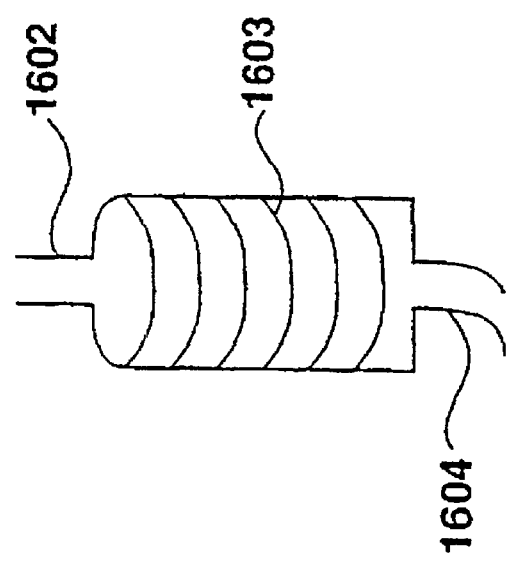

Typical metal medical devices requiring improved blood-compatibility are shown in FIGS. 16(*a*) to 16(*c*). FIG. 16(*a*) illustrates a coronary stent made from a metal mesh. Stents are used as inserts in blood vessels to improve the flow of blood through said vessels where a blockage has formed. Traditionally stents are metallic devices that are not biodegradable. Some types of stent are made of criss-crossed wire 1601 which facilitates mechanical flexibility with a vessel wall together with reduced hindrance for endothelialisation around the stent. However problems remain with the use of stents in relation to their poor blood-compatibility properties. The present invention improves the blood-compatibility of the surface of the metal stent and thus provides for a stent which can be left in place in a given blood vessel for a much longer time. Many types of metal stents exist, some being used in the coronary arteries (coronary stents) and others being used peripherally (peripheral stents). Various types exist including for example:

coilspring stents, thermal shaped memory alloy stents, self expanding steel spiral stents, self expandable stainless steel mesh stents and balloon expanding stents comprising interdigitating coils.

All practical metallic stents, such as those listed, are suitable for treatment in accordance with the present invention.

FIG. 16(*b*) illustrates a metallic medical device which is used externally to the body. The device illustrated is a heat exchanger wherein blood enters the device through inlet 1602 and is circulated around the internal mechanism 1603 before leaving the device via outlet 1604. The internal mechanism 1603 is placed directly into contact with blood circulating through the device. The present invention facilitates the interaction of the blood with the internal mechanism 1603, thus reducing problems associated with blood coagulation.

FIG. 16(*c*) shows a further metallic medical device, a guide wire 1605, as typically used in PTCA. Guide wires of this type are used to insert a balloon into a blood vessel wherein a portion of the vessel wall is restricting blood flow through for example deposited material or plaque. Insertion of a balloon located by a guide wire such as guide wire 1605 is improved in accordance with the present invention. The improvement arises because the guide wire comes into contact with blood and is hindered in its movement due to blood coagulation. The present invention improves the biocompatibility and lubricity of the surface of the guide wire and thus facilitates the overall surgical process of treating the vessel walls.

The present invention is further illustrated by the following examples of laboratory scale treatment of metal surfaces. The examples given relate to stainless steel and Nitinol, but the invention is not limited to the treatment of these two metals. The invention is suitable for treatment of a wide range of metal surfaces. Furthermore the examples given each incorporate usage of a single type of vinylfunctional silane molecule, but in practice several could be used for functionalisation of a given metal surface. The examples illustrate use of monomeric, polymeric and oligomeric vinylfunctional silane molecules. The invention is not limited to improved compatibility of metal articles with blood. It is suitable in general for improving the performance of many metal articles with biological materials, another important example being the reduction of bacterial adhesion to certain medical devices.

PREPARATIVE EXAMPLE

Production of Heparin Macromers

Heparin macromers were produced by the amidation of carboxyl groups in heparin with amino monomers of the formula set out below, in which n=3, 6 and 12 in aqueous solution with the aid of the condensing agent 1-ethyl-3-(2-dimethylaminopropyl) carbodiimide (EDC) as described by C. H. Bamford and K. G. Al-Lamee, Chemical Methods for Improving the Haemocompatibility of Synthetic Polymers, Clinical Materials, 10 (1992), 243–261.

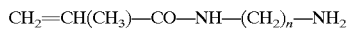

Heparin (1.0 g, purchased from Sigma, Dorset, UK) was dissolved in de-ionised water (8.3 ml) and EDC (0.33 g was added). The pH was adjusted to between 5 and 6, and after 30 minutes aminopropyl methacrylamide (0.35 g) was added. The mixture was maintained at room temperature for 17 hours with mixing by means of a Spiramix roller mixer. The pH was raised to 8 by addition of sodium hydroxide and the solution was then poured into methanol. Heparin macromer (about 0.7 g) precipitated and was isolated by filtration. The incorporation of $CH_2=CH(CH_3)$— groups into the precipitated heparin was confirmed by NMR spectroscopy.

The above procedure was repeated using the monomers in which n=6 and n=12 with similar results. Each of the three resulting heparin macromers may be co-polymerised to form a coating on a metal or ceramics substrate having on its surface an oxide film or hydroxyl groups using the procedures described below. However, the monomer in which n=3 is preferred on the grounds of availability and efficiency of participation in coupling reactions in aqueous solvents.

Example 1

Treatment of Stainless Steel using a Siloxane Oligomer Covalently Bonded to the Surface (a) Functionalisation Two samples of stainless steel were cleaned with a solution of sodium bicarbonate (1% w/v) at 60° C. for one hour and then washed with hot water. The samples were then dried at room temperature and reacted at room temperature for 2 hours with 1% vinylmethoxysiloxane oligomer (Fluorochem Limited, Old Glossop, Derbyshire, PS078.9) in toluene containing ten drops of acetic acid. The samples were washed successively with methanol and water before being subjected to polymerisation.

(b) Polymerisation

A treated surface was formed on the functionalised stainless steel samples by graft polymerisation at room temperature for 3 hours with acrylamide (10% w/v) and heparin macromer (modified heparin, 0.2% w/v) in aqueous medium using sodium thiosulphate (0.1% w/v) and ammonium persulphate (0.1% w/v). The solution was flushed with nitrogen before the graft polymerisation was carried out. The samples were then carefully washed with water before being biologically tested using the APTT-FS test.

(c) Activated Partial Thromboplastin Time-Fs (APTT-FS)

The APTT test has been widely used to monitor the effectiveness of heparin, where the clotting time is prolonged in proportion to the amount of available heparin. In the present test, a small sample of stainless steel treated with heparin, as described above, was placed in a test tube containing 200 micro-litres of plasma and incubated for one minute at 37° C. The size of the stainless steel sample used was 4 mm×4 mm. Following incubation, 200 micro-litres of APTT-FS agent were added into the test tube containing the plasma and the test sample, and then incubated for a further 3 minutes at 37° C. Following this incubation period, 200 micro-litres of calcium chloride solution (20 mM) were added into the reaction mixture and simultaneously a timer was started and the clotting time recorded. The APTT results are shown in the table below:

| Sample | Mean Value of Clotting Time (seconds) |
|---|---|
| Plasma control | 37 |
| Untreated stainless steel | 9 |
| Heparin covalently coupled, hydrophilic stainless steel | 60 | d) In Vitro Bovine Blood-flow Test

Figure 17A:
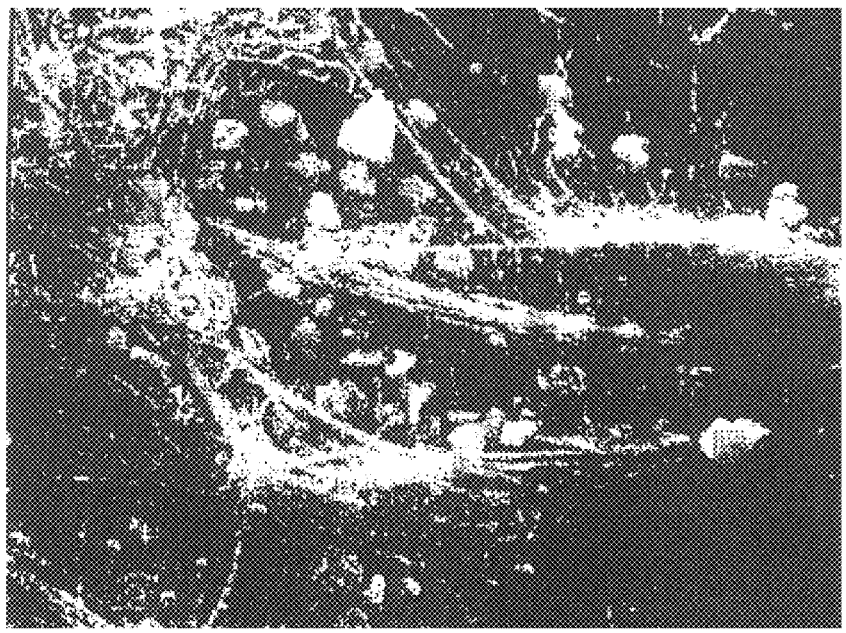
FIGS. 17(a) and 17(b) are SEM micrographs (×800) showing respectively cell and fibrin deposition on untreated stainless steel and lack of cell and fibrin deposition onto heparin-treated stainless steel according to the invention.
Figure 17B:

Bovine blood with an ACT of 200 s was circulated for 6 hours over untreated and heparin treated stainless steel using a peristaltic pump and a circulation rate of 3.5 L/min. After the circulation period the stainless steel samples were removed and washed with saline. They were then fixed with glutaraldehyde (2%) and examined by scanning electron microscopy (SEM). A sample of the re-circulated blood was tested for its ACT and exhibited no significant change from the pre-test value. A SEM micrograph of the untreated sample (FIG. 17a) showed cell and fibrin deposition onto the surface, whereas no such deposition was apparent on the hydrophilic treated and heparinised sample produced as described above (FIG. 17b). These results indicate that the present treatment gives stainless steel a significantly better haemocompatibility than the untreated material.

(e) Stability of Heparin on the Surface

The ability of heparin to remain stable and active on a treated surface was investigated by incubating the treated metal in saline at 37° C. for a week. An APTT test was then carried out which demonstrated that the covalently attached heparin was stable and retained its biological activity.

Another treated sample was allowed to remain in contact with blood for an hour so that a clot formed and became attached to the meal surface. The clot was removed by rubbing and the sample was washed under tap water. An APTT test was carried out which revealed that the clotting time remained longer than in an untreated sample.

(f) Spectroscopic Detection

An untreated sample and samples having copolymerised material with different ratios M/H of monomer to heparin macromer were prepared using the general procedure described above. The samples were extensively eluted to remove unbound and unreacted chemical species. The atomic ratios of C/O, N/O and S/O were measured by X-ray photoelectron spectroscopy (XPS) with the following results

| Sample | M/H | C/O | N/O | S/O |
|---|---|---|---|---|
| Untreated stainless steel (control) | — | 0.56 | 0.00 | 0.00 |
| Treated stainless steel | 1:1 | 1.41 | 0.06 | 0.04 |
| Treated stainless steel | 2:1 | 1.64 | 0.14 | 0.05 |

Example 2

Coating a Nickel/titanium Alloy using a Silane Covalently Bonded to the Surface (a) Functionalisation Two samples of Nitinol were cleaned with a solution of sodium bicarbonate (1% w/v) at 60° C. for one hour and then washed with hot water. The samples were then dried at room temperature before being reacted at room temperature for 12 hours with 3-(trimethoxysilyl)propyl methacrylate (Aldrich Chemical Company; 10% in hexane containing ten drops of acetic acid). The samples were washed with methanol and water successively before being subjected to polymerisation.

(b) Polymerisation

A treated surface was formed on the functionalised Nitinol samples by graft polymerisation at room temperature for 3 hours with acrylamide (10% w/v) and heparin macromer (modified heparin, 0.2% w/v) in aqueous medium using sodium thiosulphate (0.1% w/v) and ammonium persulphate (0.1% w/v). The solution was flushed with nitrogen before the graft polymerisation was carried out The samples were then carefully washed with water before biologically tested using the APTT-FS test.

(c) Activated Partial Thromoplastin Time-FS

| Sample | Mean Value of Clotting Time (seconds) |
|---|---|
| Plasma control | 35 |
| Untreated stainless steel | 8 |
| Heparin covalently coupled, hydrophilic stainless steel | 61 |

Example 3

Formation of Covalently Bound Material and Subsequent Attachment of Heparin.

(a) Functionalisation

Two samples of stainless steel were cleaned with a solution of sodium bicarbonate (1% w/v) at 60° C. for one hour and then washed carefully with hot water.

The samples were then dried at room temperature before being reacted with 1% Triethoxysilyl-modified polybutadiene (Fluorochem Limited, PS078.6) in toluene containing ten drops of acetic acid at room temperature for 2 hours. The samples were washed with methanol and water respectively before being subjected to polymerisation.

(b) Polymerisation

A treated surface was formed on the functionalised stainless steel samples by graft polymerisation at room temperature for 3 hours with acrylamide (10% w/v) and 3-aminopropyl methacrylamide (0.1% w/v) heparin macromer in aqueous medium using sodium thiosulphate (0.1% w/v) and ammonium persulphate (0.1% w/v). The solution was flushed with nitrogen before the graft polymerisation was carried out. The samples were then carefully washed with water before being coupled with 0.1% unmodified heparin (Fluka Chemical Company), and 0.03% w/v 1-ethyl-3-(-3-dimethyl amino propyl) carbodimide hydrochloride (pH 4–5) at room temperature for 6 hours. The samples were then washed carefully with water before biologically tested using APTT-FS.

(c) Activated Partial Thromboplastin Time-FS

| Sample | Mean Value of Clotting Time (seconds) |
|---|---|
| Plasma control | 34 |
| Untreated stainless steel | 10 |
| Heparin covalently coupled, hydrophilic stainless steel | 73 |

Example 4

Attachment of Additional Compounds to Metallic Stents

Stainless steel stents were functionalised with triethoxy siloxane modified polybutadiene (Fluorochem) as described in Example 3 above.

A treated surface was then prepared on some of them by copolymerising acrylamide (10% w/v) and dipyridamole (Persantin) monomethacrylate ester (5% w/v) using azo-cyano valeric acid as initiator. The solution was flushed with nitrogen, and polymerisation was carried out at 60° C. for three hours. The samples were then washed extensively with water and methanol sequentially.

In an alternative procedure, the treated surface was prepared as described above except that there was additionally present as co-monomer heparin macromer (modified heparin, 0.2% w/v).

Stents made by each of the above two procedures were dipped in solutions of vascular endothelial growth factor (VEGF, Sigma, stock solution, 80 ng/ml) which became ionically attached to the coating.

A further group of the stents made by the above two procedures was dipped into human platelet GPIIbIIIa (Sigma, stock solution, 80 ng/ml) which became ionically attached.

Stents made as above can be sterilised e.g. using ethylene oxide and packed in a sterility-maintaining container. On implantation, the stents exhibit good haemo-compatibility and their coatng encourages growth of endothelial cells.

Example 5

Formation of Covalently Bonded Material on the Surface of Glass

A glass tube was reacted at room temperature for 30 minutes with 1% w/v triethoxysilyl-modified polybutadiene (Fluorochem Ltd) in tolyene conaining ten drops of acetic acid. The tube was then washed with methanol and water.

A graft polymer was then formed on the surface of the resulting functionalised tube using acrylamide (5% w/v) in an aqueous medium which was flushed with nitrogen. The reaction was carried out at room temperature for two hours with continued flushing with nitrogen and using sodium thiosulphate (0.1% w/v) and ammonium persulphate (0.1% w/v). A very slippery surface coating was formed which was resistant to prolonged washing with hot water.

Example 6

Polymer Coated Stent with Anti-restenosis Compound

A solution was prepared of heparin (1 g) and 1-ethyl-3 (3-dimethylaminopropyl) carbodiimide (0.15 g) in deionised water. The pH of the solution was adjusted to 5.5 and the solution was mixed for 30 minutes. N-(3-aminopropyl)-methacrylamide hydrochloride was added to the solution which was then mixed overnight, after which the solution was added dropwise into stirred methanol (100 ml). Heparin macromer precipitated out and was allowed to settle. The mixture was then filtered under reduced pressure, and the resulting solid was collected and stored under refrigeration.

A 2% solution was prepared of triethoxysilyl modified polybutadiene (1.77 g) in toluene (85.5 g, and a stent was placed in this solution followed by three drops of acetic acid. After 15 minutes the stent was removed from the solution and oven dried at 80° C. for 15 minutes.

A solution was prepared of dimethyl(methacryloxyethyl) (3-sulfopropyl) ammonium betaine (SPE) (5.25 g; from Raschig), sodium thiosulphate (0.11 g) and ammonium persulphate (0.11 g) in deionised water (100 g). The above treated stent was placed in the solution together with the heparin macromer, and nitrogen was bubbled through the solution for two hours. The stent was removed, washed with 0.01 N sodium hydroxide solution and rinsed with deionised water. It was then placed in a solution of mitoxanthrone (2 mg/ml) in a selaed test tube and placed on a Spiramix for 30 minutes. The stent was removed from the solution and oven dried at 40° for 2 hours.

Evaluation of the Coated Stent

Human atherosclerotic plaque material from femoral and iliac arteries (HPPSMC) and human coronary media smooth muscle cells (HCMSMC) of passages two and three were used for the investigations. After reaching a sufficient cell number HPPSMC and HCMSMC were seeded into 6-well plates at a density of $3-4 \times 10^3$ cells/cm$^2$. One day after the cells had been seeded, a coated stent prepared as above was cut into pieces of average weight 20 mg and added to the HPPSMC and HCMSMC cultures. Due to the concave shape of the 24-well plates, movements of the stent pieces were limited. During the following stages of the test, the culture plates were moved as little as possible in order to keep the shear forces between the stent struts and the cell layer to a minimum. After three days the culture medium was exchanged, and after a further two days the stent pieces were removed. The cells were washed twice with phosphate buffered saline (PBS, Gibco, Germany) and detached by treatment with trypsin/ethylenediaminetetraacetic acid (trypsin/EDTA, Bio Whittaker). The cell numbers were measured for HCMSMC and used to determine % proloferation. Control values, values for an untreated stent, and values for the coated and mitoxantrone-containing stent described herein are shown in FIG. 18. The data shows significant inhibition of cell proliferation in the case of the mitoxantron-coated stent. FIG. 19 shows % proliferation of HCMSMC for stents which had been treated as described above except that the concentration in the solution used to treat the stent was varied. Minimal proliferation was observed when the concentration was 0.2 μg/ml.

What is claimed is:

1. A method of treating a metal, glass or ceramics article having at its surface oxide or hydroxide to enhance the bio-compatibility and/or physical characteristics of the surface, said method comprising the steps of:

priming said surface by means of functional molecules each of which has at least one alkoxysilane group which can form at least one first covalent bond by reaction with the oxide or hydroxide of said surface and at least one other group which can participate in free-radical polymerization, the priming being carried out by contacting said surface in an aprotic organic solvent substantially in the absence of water with said functional molecules and with an acid catalyst for forming said first covalent bond; and forming chains covalently attached to said other group of the functional molecules by free-radical polymerisation of at least one polymerizable monomer which imparts hydrophilic properties to said chain.

2. The method of claim 1, wherein said article is a coronary stent, peripheral stent, heat exchanger for use in conjunction with biological material, guide wire for use in angioplasty, artificial heart valve, device for storage and/or transfer of biological material, or other medical device.

3. The method of claim 2, wherein said article is one of the following stents:

a coil spring stent;

a thermal shaped memory alloy stent;

a self-expanding steel spiral stent;

a self-expandable stainless steel mesh stent;

a balloon expanding stent comprising inter-digitating coils.

4. The method of claim 1, wherein the article is of stainless steel or nitanol.

5. The method of claim 1, wherein said functional molecules have olefinically unsaturated groups.

6. The method of claim 5, wherein the functional molecules are of any of the formulae:

or

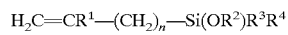

wherein $R^1$ represents a hydrogen atom or an alkyl group, $R^2$, $R^3$ and $R^4$ represent an alkyl group and n is 0 or is a positive integer.

7. The method of claim 6, wherein $R^1$ represents hydrogen, methyl or ethyl and $R^2$, $R^3$ and $R^4$ represent methyl or ethyl and the value of n is from 0 to 6.

8. The method of claim 7, wherein the functional molecule is a trialkoxysilane.

9. The method of claim 5, wherein the functional molecules comprise a $[-Si-O-]_n$ chain, wherein n is greater than 1, having alkoxy groups directly attached to the silicon atoms and having olefinically unsaturated groups attached directly or via linking groups to the silicon atoms.

10. The method of claim 9, wherein the functional molecules have vinyl and alkoxy groups attached to the silicon atoms of the chain.

11. The method of claim 5, wherein the functional molecules have:

an oligomeric or polymeric chain of carbon atoms which may include nitrogen or oxygen atoms;

one or more alkoxysilane or alkylalkoxysilane groups attached to the chain for forming covalent bonds with oxide or hydroxide of the surface; and one or more olefinically unsaturated groups which can participate in free radical polymerisation.

12. The method of claim 11, wherein the functional molecules have trialkoxysilane groups.

13. The method of claim 5, wherein said functional molecules include one or more of:

3-(trimethoxysilyl) propyl methacrylate;

vinylmethoxysilane oligomer;

diethoxymethylsilyl-modified polybutadiene; and triethoxymethylsilyl-modified polybutadiene.

14. The method of claim 1, wherein said free-radical polymerisation includes polymerising a plurality of different polymerisable molecules.

15. The method of claim 1, wherein said polymer chains include molecular units derived from acrylamide.

16. The method of claim 1, wherein at least one type of said polymerisable molecule provide means for bonding to a bio-active molecule.

17. The method of claim 16, wherein said bonding means is an amine group.

18. The method of claim 17, wherein said amine group is provided by 3-aminopropyl methacrylamide.

19. The method of claim 16, wherein said bonding means is a carboxyl group.

20. The method of claim 16, wherein said bonding means is a hydroxyl group.

21. The method according to claim 14, wherein at least one type of said polymerisable molecules is a bio-active molecule which has been modified to contain a polymerisable group.

22. The method of claim 16, wherein said bio-active molecule is an anticoagulant or anti-platelet agent.

23. The method of claim 22, wherein said anticoagulant is heparin.

24. The method of claim 22, wherein said anticoagulant is hirudin.

25. The method of claim 22, wherein said anti-platelet agent is prostaglandin or an analog thereof.

26. The method of claim 1, wherein said surface is a metal surface and said treatment of a metal surface is conducted substantially at room temperature.

27. The method of claim 1, comprising the further step of attaching to the coated stent a compound which inhibits smooth cell proliferationand/or restenosis.

28. The method of claim 27, wherein the compound is mitoxantrone or a pharmaceutically acceptable salt thereof.

29. The method of claim 1, comprising the additional step of sterilizing the article and optionally packing the article in a sterility-preserving container or wrapper.

30. The method of claim 1, wherein said article is an endovascular prosthesis, peripheral stent, heat exchanger for use in conjunction with biological material, guide wire for use in angioplasty, artificial heart valve, device for storage and/or transfer of biological material, or other medical device.

* * * * *